(12) United States Patent
Butler et al.

(10) Patent No.: US 7,867,164 B2
(45) Date of Patent: Jan. 11, 2011

(54) WOUND RETRACTOR SYSTEM

(75) Inventors: John Butler, Blackrock (IE); Trevor Vaugh, County Offaly (IE); Frank Bonadio, Bray (IE)

(73) Assignee: Atropos Limited, County Wicklow (IE)

( * ) Notice: Subject to any disclaimer, the term of this patent is extended or adjusted under 35 U.S.C. 154(b) by 519 days.

(21) Appl. No.: 10/665,395

(22) Filed: Sep. 22, 2003

(65) Prior Publication Data

US 2004/0092796 A1    May 13, 2004

Related U.S. Application Data

(63) Continuation-in-part of application No. 10/374,523, filed on Feb. 27, 2003, now Pat. No. 7,445,597, which is a continuation of application No. 09/849,341, filed on May 7, 2001, now Pat. No. 6,582,364, which is a continuation of application No. 09/688,138, filed on Oct. 16, 2000, now Pat. No. 6,254,534, application No. 10/665,395.

(60) Provisional application No. 60/490,909, filed on Jul. 30, 2003.

(30) Foreign Application Priority Data

| Oct. 14, 1999 | (IE) | ................................. 990861 |
| Dec. 16, 1999 | (IE) | ................................. 991053 |
| Feb. 18, 2000 | (EP) | ................................. 00650010 |
| Sep. 19, 2002 | (IE) | ................................. 2002/0754 |

(51) Int. Cl.
*A61B 1/32* (2006.01)

(52) U.S. Cl. .................................................. 600/208

(58) Field of Classification Search ................. 600/184, 600/185, 201–210; 128/846, 849, 850, 851, 128/852, 856
See application file for complete search history.

(56) References Cited

U.S. PATENT DOCUMENTS

| 1,157,202 | A | 10/1915 | McLeland |
| 1,598,284 | A | 8/1926 | Kinney |
| 1,810,466 | A | 6/1931 | Deutsch |
| 2,219,564 | A | 10/1940 | Reyniers |
| 2,305,289 | A | 12/1942 | Coburg |

(Continued)

FOREIGN PATENT DOCUMENTS

DE    37 39 532    12/1988

(Continued)

OTHER PUBLICATIONS

Original Specification of U.S. Appl. No. 11/486,383, filed Jul. 14, 2006.

(Continued)

*Primary Examiner*—Anu Ramana
(74) *Attorney, Agent, or Firm*—Finnegan, Henderson, Farabow, Garrett & Dunner, LLP

(57) ABSTRACT

A wound retractor system comprises a retractor having a distal ring 91 and a retracting sleeve 4 extending from the ring. An insertion tool 120 has a distal groove 122 to hold the ring for insertion of the ring through a small incision 90 in the abdominal wall 97. The retractor may be used for retracting an incision to receive an instrument therethrough. A seal or valve may be mounted to the retractor through which an instrument can pass.

25 Claims, 33 Drawing Sheets

U.S. PATENT DOCUMENTS

| | | | |
|---|---|---|---|
| 2,695,608 A | 11/1954 | Gibbon | |
| 2,835,253 A | 5/1958 | Borgeson | |
| 2,853,075 A | 9/1958 | Hoffman | |
| 3,039,468 A | 6/1962 | Price | |
| 3,111,943 A | 11/1963 | Orndorff | |
| 3,244,169 A | 4/1966 | Baxter | |
| 3,253,594 A | 5/1966 | Matthews et al. | |
| 3,313,299 A | 4/1967 | Spademan | |
| 3,329,390 A | 7/1967 | Hulsey | |
| 3,332,417 A | 7/1967 | Blanford et al. | |
| 3,347,226 A | 10/1967 | Harrower | |
| 3,347,227 A | 10/1967 | Harrower | |
| 3,397,692 A | 8/1968 | Creager, Jr. et al. | |
| 3,402,710 A | 9/1968 | Paleschuck | |
| 3,447,533 A | 6/1969 | Spicer | |
| 3,522,800 A | 8/1970 | Lesser | |
| 3,523,534 A | 8/1970 | Nolan | |
| 3,570,475 A | 3/1971 | Weinstein | |
| 3,656,485 A | 4/1972 | Robertson | |
| 3,685,786 A | 8/1972 | Woodson | |
| 3,717,151 A | 2/1973 | Collett | |
| 3,729,006 A | 4/1973 | Wilder et al. | |
| 3,782,370 A | 1/1974 | McDonald | |
| 3,797,478 A | 3/1974 | Walsh et al. | |
| 3,807,393 A | 4/1974 | McDonald | |
| 3,828,764 A | 8/1974 | Jones | |
| 3,841,332 A | 10/1974 | Treacle | |
| 3,853,126 A | 12/1974 | Schulte | |
| 3,853,127 A | 12/1974 | Spademan | |
| 3,856,021 A | 12/1974 | Macintosh | |
| 3,907,389 A | 9/1975 | Cox et al. | |
| 3,915,171 A | 10/1975 | Shermeta | |
| 3,965,890 A | 6/1976 | Gauthier | |
| 3,996,623 A | 12/1976 | Kaster | |
| 4,000,739 A | 1/1977 | Stevens | |
| 4,016,884 A | 4/1977 | Kwan-Gett | |
| 4,024,872 A | 5/1977 | Muldoon | |
| 4,030,500 A | 6/1977 | Ronnquist | |
| 4,083,370 A | 4/1978 | Taylor | |
| 4,096,853 A | 6/1978 | Weigand | |
| 4,130,113 A | 12/1978 | Graham | |
| 4,177,814 A | 12/1979 | Knepshield | |
| 4,188,945 A | 2/1980 | Wenander | |
| 4,217,664 A | 8/1980 | Faso | |
| 4,228,792 A | 10/1980 | Rhys-Davies | |
| 4,239,036 A | 12/1980 | Krieger | |
| 4,240,411 A | 12/1980 | Hosono | |
| 4,253,201 A | 3/1981 | Ross et al. | |
| 4,306,562 A | 12/1981 | Osborne | |
| 4,321,915 A | 3/1982 | Leighton | |
| 4,331,138 A | 5/1982 | Jessen | |
| 4,338,934 A | 7/1982 | Spademan | |
| 4,338,937 A | 7/1982 | Lehrman | |
| 4,367,728 A | 1/1983 | Mutke | |
| 4,399,816 A | 8/1983 | Spangler | |
| 4,411,659 A | 10/1983 | Jensen et al. | |
| 4,421,296 A | 12/1983 | Stephens | |
| 4,424,833 A | 1/1984 | Spector | |
| 4,428,364 A | 1/1984 | Bartolo | |
| 4,430,081 A | 2/1984 | Timmermans | |
| 4,434,791 A | 3/1984 | Darnell | |
| 4,436,519 A | 3/1984 | O'Neill | |
| 4,485,490 A | 12/1984 | Akers et al. | |
| 4,488,877 A | 12/1984 | Klein | |
| 4,543,088 A | 9/1985 | Bootman | |
| 4,550,713 A | 11/1985 | Hyman | |
| 4,553,537 A | 11/1985 | Rosenberg | |
| 4,601,710 A | 7/1986 | Moll | |
| 4,610,665 A | 9/1986 | Matsumoto | |
| 4,626,245 A | 12/1986 | Weinstein | |
| 4,634,424 A | 1/1987 | O'Boyle | |
| 4,649,904 A | 3/1987 | Krauter | |
| 4,654,030 A | 3/1987 | Moll et al. | |
| 4,673,393 A | 6/1987 | Suzuki et al. | |
| 4,673,394 A | 6/1987 | Fenton | |
| 4,755,170 A | 7/1988 | Golden | |
| 4,776,843 A * | 10/1988 | Martinez et al. | 604/86 |
| 4,777,943 A | 10/1988 | Chvapil | |
| 4,784,646 A | 11/1988 | Feingold | |
| 4,798,594 A | 1/1989 | Hillstead | |
| 4,809,679 A | 3/1989 | Shimonaka | |
| 4,863,438 A | 9/1989 | Gauderer | |
| 4,889,107 A | 12/1989 | Kaufman | |
| 4,895,565 A | 1/1990 | Hillstead | |
| 4,897,081 A | 1/1990 | Poirier | |
| 4,903,710 A | 2/1990 | Jessamine et al. | |
| 4,950,222 A | 8/1990 | Scott et al. | |
| 4,950,223 A | 8/1990 | Trimark | |
| 4,984,564 A | 1/1991 | Yuen | |
| 4,991,593 A | 2/1991 | LeVahn | |
| 4,998,538 A | 3/1991 | Charowsky et al. | |
| 5,015,228 A | 5/1991 | Columbus et al. | |
| 5,019,101 A | 5/1991 | Purkait | |
| 5,041,095 A | 8/1991 | Littrell | |
| 5,045,070 A | 9/1991 | Grodecki et al. | |
| D320,658 S | 10/1991 | Quigley et al. | |
| 5,071,411 A | 12/1991 | Hillstead | |
| 5,074,878 A | 12/1991 | Bark et al. | |
| 5,082,005 A | 1/1992 | Kaldany | |
| 5,092,846 A | 3/1992 | Nishijima | |
| 5,092,868 A | 3/1992 | Mehdian | |
| 5,125,897 A | 6/1992 | Quinn et al. | |
| 5,141,498 A | 8/1992 | Christian | |
| 5,149,327 A | 9/1992 | Oshiyama | |
| 5,158,553 A | 10/1992 | Berry et al. | |
| 5,159,921 A | 11/1992 | Hoover | |
| 5,161,773 A | 11/1992 | Tower | |
| 5,167,636 A | 12/1992 | Clement | |
| 5,178,162 A | 1/1993 | Bose | |
| 5,188,595 A | 2/1993 | Jacobi | |
| 5,192,301 A | 3/1993 | Kamiya et al. | |
| 5,207,656 A | 5/1993 | Kranys | |
| 5,209,737 A | 5/1993 | Richartt | |
| 5,211,370 A | 5/1993 | Powers | |
| 5,211,633 A | 5/1993 | Stouder | |
| 5,213,114 A | 5/1993 | Bailey, Jr. | |
| 5,234,455 A | 8/1993 | Mulhollan | |
| 5,242,409 A | 9/1993 | Buelna | |
| 5,248,304 A | 9/1993 | Vigdorchik et al. | |
| 5,261,883 A | 11/1993 | Hood et al. | |
| 5,263,922 A | 11/1993 | Sova et al. | |
| 5,269,763 A | 12/1993 | Boehmer | |
| D343,236 S | 1/1994 | Quigley et al. | |
| 5,279,575 A | 1/1994 | Sugarbaker | |
| D346,022 S | 4/1994 | Quigley et al. | |
| 5,299,582 A | 4/1994 | Potts | |
| 5,300,036 A | 4/1994 | Mueller | |
| 5,308,336 A | 5/1994 | Hart et al. | |
| 5,309,896 A | 5/1994 | Moll et al. | |
| 5,316,541 A | 5/1994 | Fischer | |
| 5,320,611 A | 6/1994 | Bonutti | |
| 5,330,437 A | 7/1994 | Durman | |
| 5,330,497 A | 7/1994 | Freitas | |
| 5,336,192 A | 8/1994 | Palestrant | |
| 5,342,315 A | 8/1994 | Rowe et al. | |
| 5,342,385 A | 8/1994 | Norelli et al. | |
| 5,350,364 A | 9/1994 | Stephens et al. | |
| 5,364,345 A | 11/1994 | Lowery et al. | |
| 5,366,478 A | 11/1994 | Brinkerhoff et al. | |
| 5,368,545 A | 11/1994 | Schaller et al. | |
| 5,383,861 A | 1/1995 | Hempel | |
| 5,385,553 A | 1/1995 | Hart et al. | |
| 5,391,153 A | 2/1995 | Haber et al. | |
| 5,391,156 A | 2/1995 | Hildwein et al. | |

| | | | | | | |
|---|---|---|---|---|---|---|
| 5,395,309 A | 3/1995 | Tanaka et al. | | 5,957,913 A | 9/1999 | de la Torre et al. |
| 5,403,264 A | 4/1995 | Wohlers | | 5,964,781 A | 10/1999 | Mollenauer et al. |
| 5,407,433 A | 4/1995 | Loomas | | 5,993,485 A | 11/1999 | Beckers |
| 5,423,848 A | 6/1995 | Washizuka et al. | | 5,994,450 A | 11/1999 | Pearce |
| 5,429,609 A | 7/1995 | Yoon | | 5,997,515 A | 12/1999 | de la Torre et al. |
| 5,431,676 A | 7/1995 | Durbal | | 6,024,736 A | 2/2000 | de la Torre et al. |
| 5,443,452 A | 8/1995 | Hart et al. | | 6,025,067 A | 2/2000 | Fay |
| 5,456,284 A | 10/1995 | Ryan | | 6,033,426 A | 3/2000 | Kaji |
| 5,476,475 A | 12/1995 | Gadberry | | 6,033,428 A | 3/2000 | Sardella |
| 5,480,410 A | 1/1996 | Cuschieri et al. | | 6,042,573 A | 3/2000 | Lucey |
| 5,496,280 A | 3/1996 | Vandenbroeck | | 6,048,309 A | 4/2000 | Flom et al. |
| 5,503,112 A | 4/1996 | Luhman | | 6,059,816 A | 5/2000 | Moenning |
| 5,514,109 A | 5/1996 | Mollenauer et al. | | 6,077,288 A | 6/2000 | Shimomura et al. |
| 5,514,133 A | 5/1996 | Golub et al. | | 6,099,506 A | 8/2000 | Macoviak et al. |
| 5,520,632 A | 5/1996 | Leveen | | 6,110,154 A | 8/2000 | Shimomura et al. |
| 5,522,791 A | 6/1996 | Leyva | | 6,123,689 A | 9/2000 | To |
| 5,522,824 A | 6/1996 | Ashby | | 6,142,935 A | 11/2000 | Flom et al. |
| 5,524,644 A | 6/1996 | Crook | | 6,142,936 A | 11/2000 | Beane et al. |
| 5,526,536 A | 6/1996 | Cartmill | | 6,150,608 A | 11/2000 | Wambeke |
| 5,545,179 A | 8/1996 | Williamson, IV | | 6,159,182 A | 12/2000 | Davis |
| 5,562,632 A | 10/1996 | Davila | | 6,162,172 A | 12/2000 | Cosgrove et al. |
| 5,562,688 A | 10/1996 | Riza | | 6,162,196 A | 12/2000 | Hart et al. |
| 5,577,993 A * | 11/1996 | Zhu et al. ............... 600/204 | | 6,162,206 A | 12/2000 | Bindokas |
| 5,582,577 A | 12/1996 | Lund et al. | | 6,163,949 A | 12/2000 | Neuenschwander |
| 5,584,850 A | 12/1996 | Hart et al. | | 6,164,279 A | 12/2000 | Tweedle |
| 5,601,579 A | 2/1997 | Semertzides | | 6,171,282 B1 | 1/2001 | Ragsdale |
| 5,620,415 A | 4/1997 | Lucey | | 6,183,486 B1 | 2/2001 | Snow et al. |
| 5,632,979 A | 5/1997 | Goldberg | | 6,238,373 B1 | 5/2001 | de la Torre et al. |
| 5,634,911 A | 6/1997 | Hermann et al. | | 6,254,533 B1 | 7/2001 | Fadem et al. |
| 5,634,936 A | 6/1997 | Linden | | 6,254,534 B1 | 7/2001 | Butler et al. |
| 5,634,937 A | 6/1997 | Mollenauer et al. | | 6,258,065 B1 | 7/2001 | Dennis |
| 5,636,645 A | 6/1997 | Ou | | 6,315,770 B1 | 11/2001 | de la Torre et al. |
| 5,640,977 A | 6/1997 | Leahy et al. | | 6,319,246 B1 | 11/2001 | de la Torre et al. |
| 5,649,550 A | 7/1997 | Crook | | 6,322,541 B2 | 11/2001 | West |
| 5,653,705 A | 8/1997 | de la Torre et al. | | 6,346,074 B1 | 2/2002 | Roth |
| 5,657,963 A | 8/1997 | Hinchliffe | | 6,382,211 B1 | 5/2002 | Crook |
| 5,658,272 A | 8/1997 | Hasson | | 6,420,475 B1 | 7/2002 | Chen |
| 5,658,306 A | 8/1997 | Kieturakis | | 6,440,063 B1 | 8/2002 | Beane |
| 5,672,168 A | 9/1997 | de la Torre et al. | | 6,450,983 B1 | 9/2002 | Rambo |
| 5,685,854 A | 11/1997 | Green | | 6,454,783 B1 | 9/2002 | Piskun |
| 5,707,703 A | 1/1998 | Rothrum et al. | | 6,458,543 B1 | 11/2002 | Bakal |
| 5,709,664 A | 1/1998 | Vandenbroeck | | 6,488,620 B1 | 12/2002 | Segermark et al. |
| 5,720,730 A | 2/1998 | Blake, III | | 6,533,734 B1 | 3/2003 | Corley, III et al. |
| 5,738,628 A | 4/1998 | Sierocuk et al. | | 6,554,793 B1 | 4/2003 | Pauker |
| 5,741,234 A | 4/1998 | Aboul-Hosn | | 6,578,577 B2 | 6/2003 | Bonadio et al. |
| 5,741,298 A | 4/1998 | MacLeod | | 6,582,364 B2 | 6/2003 | Butler et al. |
| 5,749,882 A | 5/1998 | Hart et al. | | 6,589,167 B1 | 7/2003 | Shimomura |
| 5,755,660 A | 5/1998 | Tyagi | | 6,589,211 B1 | 7/2003 | MacLeod |
| 5,769,783 A | 6/1998 | Fowler | | 6,607,504 B2 | 8/2003 | Haarala |
| 5,782,812 A | 7/1998 | Hart et al. | | 6,613,952 B2 | 9/2003 | Rambo |
| 5,795,290 A | 8/1998 | Bridges | | 6,623,426 B2 | 9/2003 | Bonadio et al. |
| 5,803,919 A | 9/1998 | Hart et al. | | 6,706,050 B1 | 3/2004 | Giannadakis |
| 5,803,921 A | 9/1998 | Bonadio | | 6,714,298 B2 | 3/2004 | Ryer |
| 5,807,350 A | 9/1998 | Diaz | | 6,723,044 B2 | 4/2004 | Pulford |
| 5,810,721 A | 9/1998 | Mueller et al. | | 6,796,940 B2 | 9/2004 | Bonadio et al. |
| 5,813,409 A | 9/1998 | Leahy et al. | | 6,797,765 B2 | 9/2004 | Pearce |
| 5,814,026 A | 9/1998 | Yoon | | 6,814,078 B2 | 11/2004 | Crook |
| 5,817,062 A | 10/1998 | Flom | | 6,814,700 B2 | 11/2004 | Mueller |
| 5,817,111 A | 10/1998 | Riza | | 6,840,951 B2 | 1/2005 | de la Torre et al. |
| 5,820,555 A | 10/1998 | Mueller, Jr. | | 6,846,287 B2 | 1/2005 | Bonadio et al. |
| 5,832,925 A | 11/1998 | Rothrum | | 6,860,463 B2 | 3/2005 | Hartley |
| 5,853,395 A | 12/1998 | Crook et al. | | 6,866,861 B1 | 3/2005 | Luhman |
| 5,865,728 A * | 2/1999 | Moll et al. ............... 600/204 | | 6,884,253 B1 | 4/2005 | McFarlane |
| 5,871,474 A | 2/1999 | Hermann et al. | | 6,902,541 B2 | 6/2005 | McNally et al. |
| 5,882,344 A | 3/1999 | Stouder | | 6,908,430 B2 | 6/2005 | Caldwell |
| 5,899,208 A | 5/1999 | Bonadio | | 6,916,331 B2 | 7/2005 | Mollenauer et al. |
| 5,904,699 A | 5/1999 | Schwemberger et al. | | 6,936,037 B2 | 8/2005 | Bubb |
| 5,904,703 A | 5/1999 | Gilson | | 6,939,296 B2 | 9/2005 | Ewers |
| 5,906,577 A | 5/1999 | Beane et al. | | 6,945,932 B1 | 9/2005 | Caldwell et al. |
| 5,916,232 A | 6/1999 | Hart | | 6,958,037 B2 | 10/2005 | Ewers |
| 5,944,450 A | 8/1999 | Stevens | | 6,979,324 B2 | 12/2005 | Byordi |
| 5,947,922 A | 9/1999 | MacLeod | | 7,008,377 B2 | 3/2006 | Beane |
| 5,951,467 A | 9/1999 | Picha et al. | | 7,052,454 B2 | 5/2006 | Taylor |

| | | | | | | |
|---|---|---|---|---|---|---|
| 7,081,089 | B2 | 7/2006 | Bonadio et al. | FR | 1456623 | 9/1966 |
| 7,195,590 | B2 | 3/2007 | Butler et al. | GB | 1151993 | 5/1969 |
| 2001/0003791 | A1 | 6/2001 | Burbank et al. | GB | 1355611 | 6/1974 |
| 2001/0037053 | A1 | 11/2001 | Bonadio et al. | GB | 1372491 | 10/1974 |
| 2001/0039430 | A1 | 11/2001 | Dubrul et al. | GB | 1379772 | 1/1975 |
| 2002/0038077 | A1 | 3/2002 | de la Torre et al. | GB | 1400808 | 7/1975 |
| 2002/0111536 | A1* | 8/2002 | Cuschieri et al. ............ 600/210 | GB | 1407023 | 9/1975 |
| 2002/0151954 | A1 | 10/2002 | Brenneman | GB | 1496696 | 12/1977 |
| 2003/0009181 | A1 | 1/2003 | Gellman et al. | GB | 2071502 | 9/1981 |
| 2003/0073883 | A1 | 4/2003 | Stiles | GB | 2255019 | 10/1992 |
| 2003/0139756 | A1 | 7/2003 | Brustad | GB | 2275420 | 8/1994 |
| 2003/0187376 | A1 | 10/2003 | Rambo | JP | 10-108868 | 4/1998 |
| 2003/0192553 | A1 | 10/2003 | Rambo | JP | 11-290327 | 10/1999 |
| 2003/0225392 | A1 | 12/2003 | McMichael | JP | 2001-61850 | 3/2001 |
| 2004/0015185 | A1 | 1/2004 | Ewers et al. | JP | 2002-28163 | 1/2002 |
| 2004/0024363 | A1 | 2/2004 | Goldberg | JP | 2004-195037 | 7/2004 |
| 2004/0049100 | A1 | 3/2004 | Butler | SU | 1342485 | 1/1997 |
| 2004/0073090 | A1 | 4/2004 | Butler | WO | WO 86/06272 | 11/1986 |
| 2004/0092796 | A1 | 5/2004 | Butler et al. | WO | WO 92/11880 | 7/1992 |
| 2004/0093018 | A1 | 5/2004 | Johnson | WO | WO 92/21292 | 12/1992 |
| 2004/0106942 | A1 | 6/2004 | Taylor et al. | WO | WO 93/05740 | 4/1993 |
| 2004/0143158 | A1 | 7/2004 | Hart et al. | WO | WO 95/05207 | 2/1995 |
| 2004/0181246 | A1 | 9/2004 | Heppler | WO | WO 95/07056 | 3/1995 |
| 2004/0215063 | A1 | 10/2004 | Bonadio et al. | WO | WO 95/15123 | 6/1995 |
| 2004/0260246 | A1 | 12/2004 | Desmond | WO | WO 95/22289 | 8/1995 |
| 2005/0020884 | A1 | 1/2005 | Heart et al. | WO | WO 95/24864 | 9/1995 |
| 2005/0033246 | A1 | 2/2005 | Ahlberg | WO | WO 95/27445 | 10/1995 |
| 2005/0059865 | A1 | 3/2005 | Kahle et al. | WO | WO 95/27468 | 10/1995 |
| 2005/0065543 | A1 | 3/2005 | Kahle et al. | WO | WO 96/36283 | 11/1996 |
| 2005/0090713 | A1 | 4/2005 | Gozales | WO | WO 97/32514 | 9/1997 |
| 2005/0090716 | A1 | 4/2005 | Bonadio et al. | WO | WO 97/32515 | 9/1997 |
| 2005/0090717 | A1 | 4/2005 | Bonadio et al. | WO | WO 97/43958 | 11/1997 |
| 2005/0131349 | A1 | 6/2005 | Albrecht | WO | WO 98/35614 | 8/1998 |
| 2005/0148823 | A1 | 7/2005 | Vaugh et al. | WO | WO 98/48724 | 11/1998 |
| 2005/0159647 | A1 | 7/2005 | Hart et al. | WO | WO 99/03416 | 1/1999 |
| 2005/0192483 | A1 | 9/2005 | Bonadio et al. | WO | WO 99/25268 | 5/1999 |
| 2005/0192598 | A1 | 9/2005 | Johnson | WO | WO 99/29250 | 6/1999 |
| 2005/0203346 | A1 | 9/2005 | Bonadio et al. | WO | WO 00/32116 | 6/2000 |
| 2005/0240082 | A1 | 10/2005 | Bonadio et al. | WO | WO 00/32117 | 6/2000 |
| 2005/0241647 | A1 | 11/2005 | Nguyen | WO | WO 00/32119 | 6/2000 |
| 2005/0277946 | A1 | 12/2005 | Greenhalgh | WO | WO 00/32120 | 6/2000 |
| 2005/0288558 | A1 | 12/2005 | Ewers | WO | WO 00/35356 | 6/2000 |
| 2005/0288634 | A1 | 12/2005 | O'Herron | WO | WO 00/54675 | 9/2000 |
| 2006/0041270 | A1 | 2/2006 | Lenker et al. | WO | WO 00/54676 | 9/2000 |
| 2006/0047284 | A1 | 3/2006 | Gresham | WO | WO 00/54677 | 9/2000 |
| 2006/0106402 | A1 | 5/2006 | McLucas | WO | WO 01/08563 | 2/2001 |
| 2006/0149137 | A1 | 7/2006 | Pingleton et al. | WO | WO 01/08581 | 2/2001 |
| 2006/0149306 | A1 | 7/2006 | Hart et al. | WO | WO 01/26558 | 4/2001 |
| 2006/0247498 | A1 | 11/2006 | Bonadio et al. | WO | WO 01/54588 A1 | 8/2001 |
| 2006/0247499 | A1 | 11/2006 | Butler et al. | WO | WO 01/91652 | 12/2001 |
| 2009/0036745 | A1 | 2/2009 | Bonadio et al. | WO | WO 02/34108 A2 | 5/2002 |
| 2009/0149714 | A1 | 6/2009 | Bonadio | WO | WO 03/026512 A1 | 4/2003 |
| 2009/0326330 | A1 | 12/2009 | Bonadio et al. | WO | WO 03/034908 A3 | 5/2003 |
| | | | | WO | WO 03/061480 A1 | 7/2003 |
| | | | | WO | WO 03/103548 A1 | 12/2003 |
| | | | | WO | WO 2004/026153 A1 | 4/2004 |
| | | | | WO | WO 2004/030547 A1 | 4/2004 |
| | | | | WO | WO 2005/009257 A2 | 2/2005 |

FOREIGN PATENT DOCUMENTS

| | | |
|---|---|---|
| DE | 37 37 121 | 5/1989 |
| DE | 296 00 939 | 6/1998 |
| DE | 199 15 061 | 10/2000 |
| EP | 0142262 | 5/1985 |
| EP | 0537768 | 4/1993 |
| EP | 0950376 | 10/1999 |
| EP | 1118657 | 7/2001 |
| EP | 1 500 382 A1 | 1/2005 |
| EP | 1 520 544 A1 | 4/2005 |

OTHER PUBLICATIONS

Kagaya, "Laparoscopic cholecystectomy via two ports, using the "Twin-Port" system", J. Hepatobiliary Pancreat Surg (2001) 8:76-80.

* cited by examiner

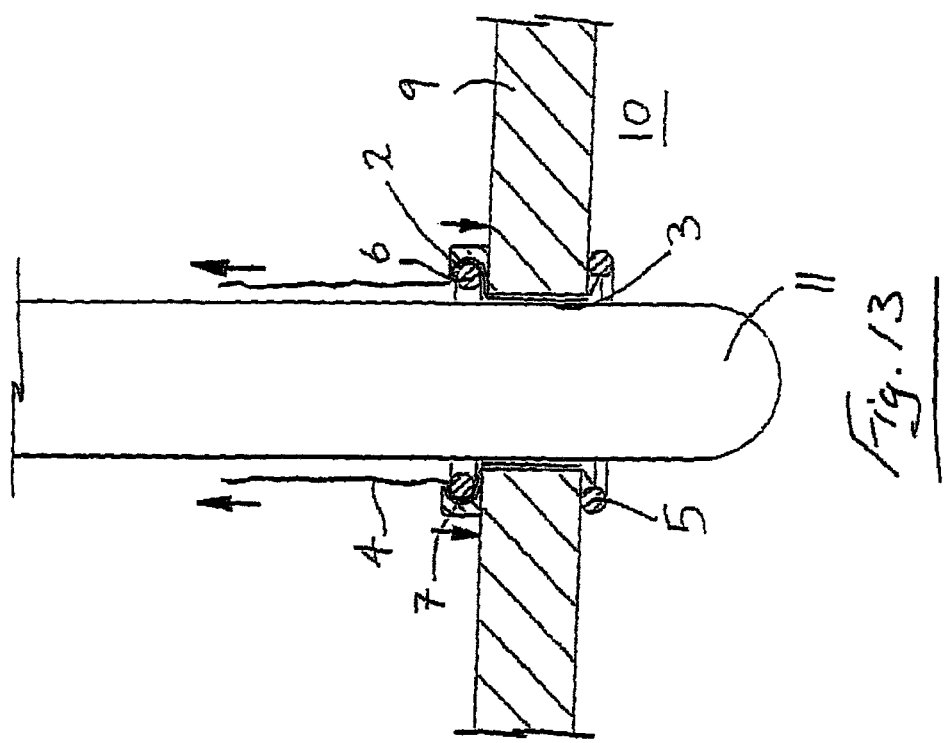
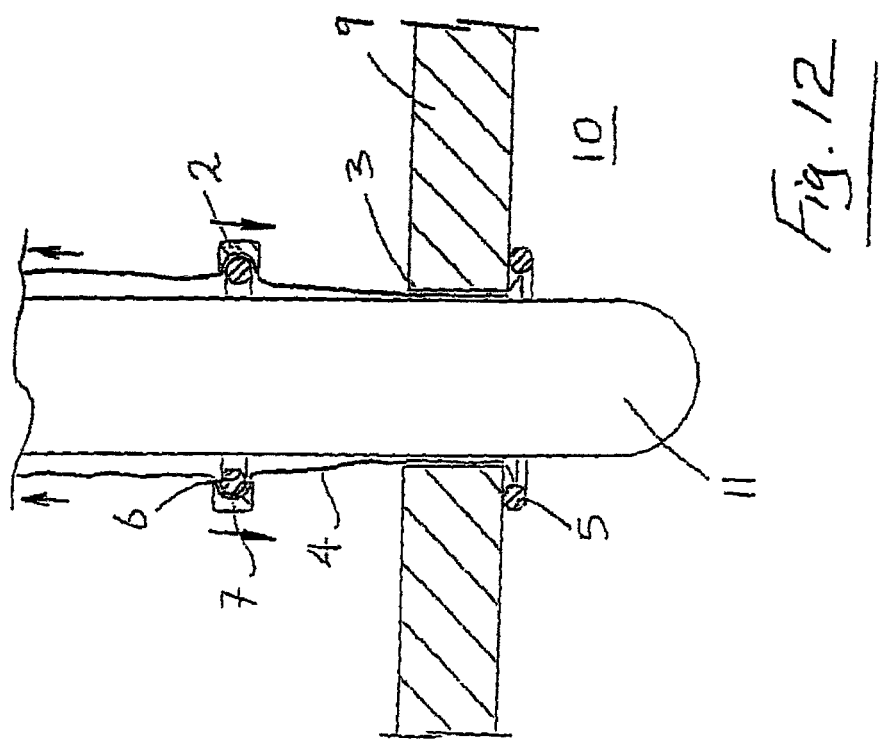

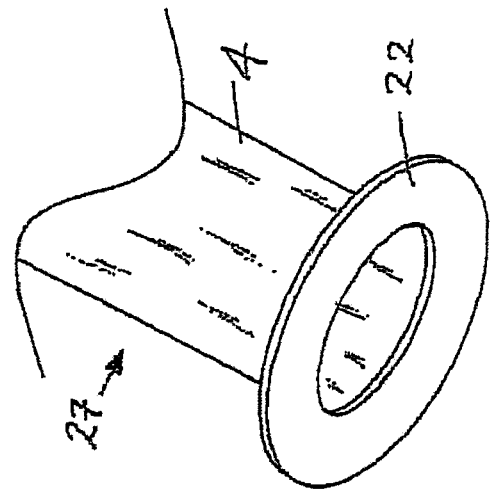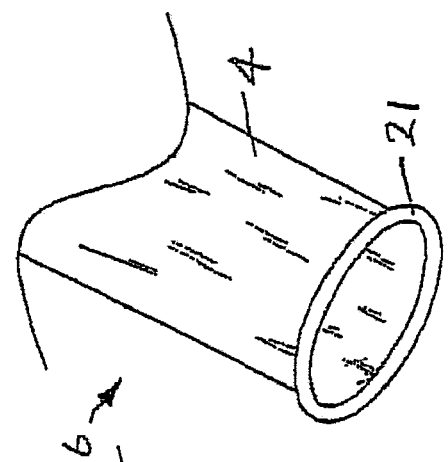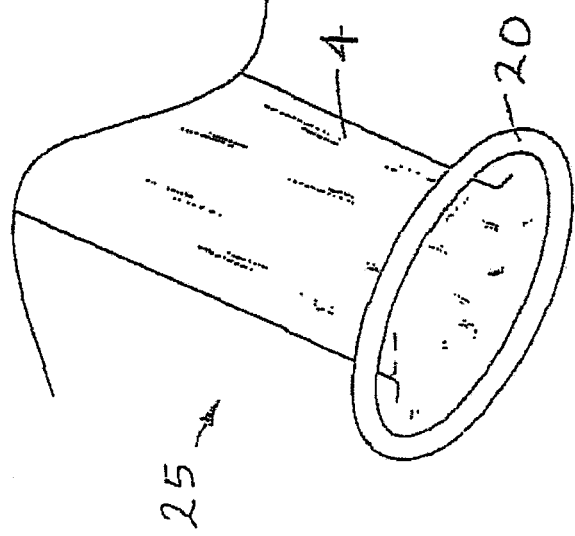

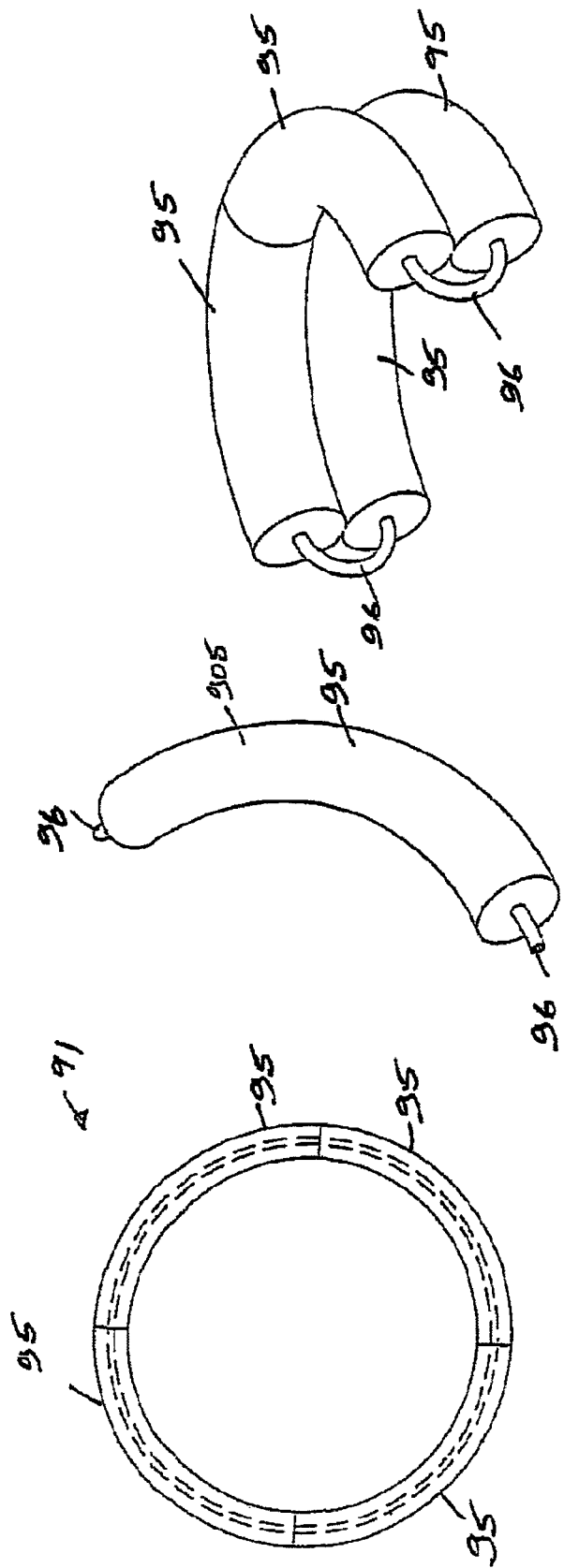

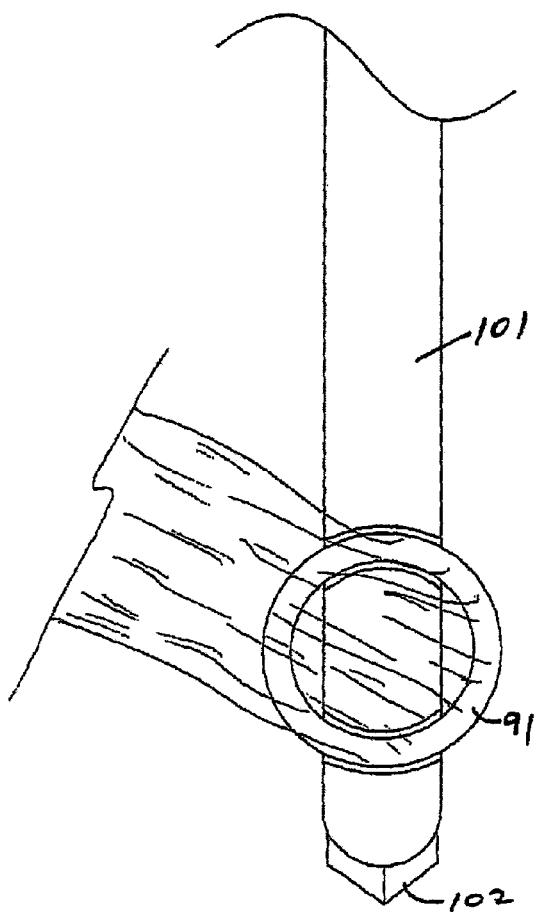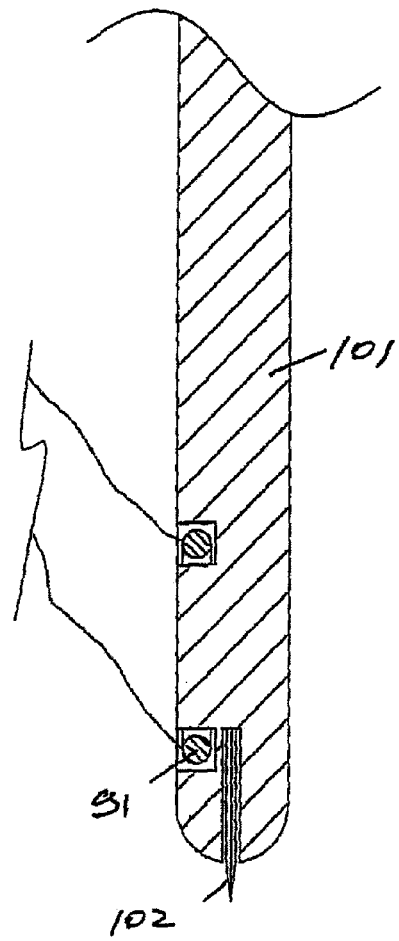
Fig. 34
Fig. 35

WOUND RETRACTOR SYSTEM

This application is a Continuation-in-Part of U.S. Ser. No. 10/374,523 filed Feb. 27, 2003, which is a continuation of application Ser. No. 09/849,341, filed on May 7, 2001, now U.S. Pat. No. 6,582,364, which is a continuation of application Ser. No. 09/688,138, filed Oct. 16, 2000, now U.S. Pat. No. 6,254,534. This application cairns the priority of Ireland Application No. 990861, filed Oct. 14, 1999, Ireland Application No. 991053, filed Dec. 16, 1999, European Application No. 00650010, filed Feb. 18, 2000, Ireland Application No. 2002/0754, filed Sep. 19, 2002, and also claims the benefit of U.S. Provisional Application Nos. 60/401,023, filed on Aug. 6, 2002, and 60/490,909, filed on Jul. 30, 2003.

This invention relates to a wound retractor suitable for retracting the sides of wound opening laterally.

Conventional practice in keyhole or Laparoscopic Surgery uses a trocar to allow the insertion of an instrument into a body cavity such as the abdomen for carrying out a procedure. In carrying out such procedures it is known to insufflate the abdomen to create a working space between the anterior abdominal wall and the viscera. There are a number of problems with the use of conventional trocars. One of the problems with the use of conventional instrument insertion systems is that there is a risk of loss of gas pressure through the margins of the incision. The problem is even more pronounced if an initial incision is made before a first trocar is introduced. Another problem is that typical trocars will extend at least 50 mm into the abdominal cavity taking up precious space. Still another limitation of the conventional trocar is the fact that these long narrow fixed diameter rigid tubes limit both the type of instrument one can use through them, as well as restricting the manoeuvrability of the instrument.

This invention is directed towards providing a retractor system and method which will address at least some of these issues.

STATEMENTS OF INVENTION

According to the invention there is provided a wound retractor system comprising:
- a retractor having a retracting member for insertion into a wound opening; and
- an insertion tool for inserting or assisting the insertion of or deployment of the retracting member in a wound opening.

In one embodiment the insertion tool has a receiver for mounting the retractor to the insertion device.

The retractor may comprise a distal portion and the receiver is adapted for mounting the distal portion to the insertion tool. The receiver may comprise a groove for receiving the distal portion of the retractor. In one embodiment the distal portion comprises a distal ring member mounted to the retracting member. The distal ring member may be of flexible material. The ring member may be of elastomeric material.

In one embodiment the insertion tool comprises an elongate member having a distal end. The distal end of the insertion tool may have a cutting blade for forming an incision.

In one embodiment the retractor comprises a proximal ring member and the insertion tool has a pusher to push the proximal member towards a distal member to shorten the axial extent between the proximal and distal ring members. The pusher may comprise a blade.

The insertion tool comprises a stop for limiting the extent to which the tool may be inserted through an opening. The stop may be adjustably mounted on the insertion tool.

In one embodiment the insertion tool comprises a handle.

The insertion tool may have a wound extending portion with a transverse dimension of from 3 to 35 mm, preferably from 5 to 12 mm.

The invention also provides a wound retractor which comprises
- a proximal member for location externally of a wound opening;
- the proximal member being movable relative to the retracting member to shorten the axial extent of the retracting member to laterally retract a wound opening.

The wound retractor may form part of the system of the invention.

The proximal member may comprise an annular ring means. The annular ring means may comprise an inner ring and an outer ring between which the retracting member may be led.

In one embodiment one of the rings defines a projection for location in a complimentary recess of the outer ring with the retracting member located therebetween. The projection may be a relatively tight fit in the recess to grip the retracting member therebetween. The projection may be locatable in the recess in a snap-fit manner. In one case the inner ring defines the projection and the outer ring defines the recess. Alternatively, the outer ring defines the projection and the inner ring defines the recess.

A system may comprise one or more valves to facilitate sealed access of an object through the retractor. The valve(s) maybe mounted to the proximal member.

In one embodiment the retractor comprises a distal member coupled to a distal end of the retracting member. The distal member may comprise an O-ring.

The distal member may comprise an annular disc.

The distal member may be of a resilient material.

The retracting member may be flared distally outwardly.

The retractor may comprise means to seal a retracted wound opening. The sealing means may be provided externally of a wound opening. The sealing means may be mountable to the proximal member. The sealing means may comprise a cap.

The sealing means may comprise a valve to facilitate sealed access of an object through the sealing means. The object may comprise an instrument.

In one embodiment the retracting member comprises a sleeve to line a wound opening.

The invention also provides a method for introducing an element such as an instrument into a body cavity, the method comprising the steps of:
- making an incision in a body wall, the incision having a length to accommodate the element on retraction of the incision;
- providing a wound retractor comprising a distal member, a proximal member and a retracting member extending at least between the distal member and the proximal member, the retracting member being axially movable relative to the proximal member;
- inserting the distal member through the incision such that the retracting member extends through the incision and the proximal member is located outside of the incision;
- moving the proximal member relative to the retracting member to shorten the axial extent of the retracting member located between the distal member and the proximal member;

providing a valve;
mounting the valve to the reactor;
introducing an element through the valve; and
introducing the element through the retracted incision and into the body cavity.

Typically the body cavity is an abdominal cavity.

The length of the incision may be from 3 to 35 millimetres, typically from 5 to 15 mm.

In another aspect the invention provides a method for retracting an incision comprising the steps of:
making an incision in a body wall;
providing a wound retractor comprising a distal member and a retracting member extending from the distal member;
providing an insertion tool having a receiver for the retractor;
mounting the retractor to the receiver of the insertion tool;
inserting the insertion tool with the retractor mounted thereon through the incision;
deploying the retractor in the incision; and
withdrawing the insertion tool from the incision.

In one embodiment the retracting member comprises a proximal portion located proximally of the proximal member and a distal portion located distally of the proximal member, and the method comprises the step of decoupling the proximal portion from the distal portion after retraction of the wound opening. The proximal portion may be decoupled from the distal portion by a cutting action.

In one embodiment the proximal member comprises an inner ring and an outer ring, and the method comprises the step of fitting the inner ring relative to the outer ring to grip the retracting member therebetween. The inner ring may be snap-fitted relative to the outer ring after retraction of the wound opening. The inner ring may be fitted relative to the outer ring after retraction of the wound opening.

The method may comprise the step of snap-fitting the inner ring relative to the outer ring which decouples the proximal portion of the retracting member from the distal portion.

In embodiment the method comprises the step of mounting the retractor to an insertion tool, and the insertion tool is inserted into the wound opening to insert the retractor into the wound opening.

The incision may be made by the insertion tool.

The method may comprise the step of sealing the retracted wound opening.

In another aspect the invention provides a wound retractor comprising:
a retracting member for insertion into a wound opening; and
a proximal member for location externally of a wound opening;

the proximal member being movable relative to the retracting member to shorten the axial extent of the retracting member to laterally retract a wound opening.

In one embodiment the proximal member comprises an annular ring means.

In one case the annular ring means comprises an inner ring and an outer ring between which the retracting member may be lead. One of the rings may define a projection for location in a complimentary recess of the outer ring with the retracting member located therebetween. The projection may be a relatively tight fit in the recess to grip the retracting member therebetween. In one arrangement the projection is locatable in the recess in a snap-fit manner.

In one embodiment the inner ring defines the projection and the outer ring defines the recess.

Alternatively the outer ring defines the projection and the inner ring defines the recess.

In one embodiment the proximal member comprises one or more valves to facilitate sealed access of an object through the proximal member.

In an aspect of the invention the retractor comprises a distal member coupled to a distal end of the retracting member. The distal member may comprise an O-ring. Alternatively the distal member comprises an annular disc. The distal member may be of a resilient material.

In one embodiment the retracting member is flared distally outwardly.

In one aspect the retractor comprises means to seal a retracted wound opening. The sealing means may be provided externally of a wound opening.

Typically, the sealing means is mountable to the proximal member. The sealing means may comprise a cap.

In one embodiment the sealing means comprises one or more valves to facilitate sealed access of an object through the sealing means.

In one arrangement the retracting member comprises a sleeve to line a wound opening.

The invention also provides a method of retracting a wound opening, the method comprising the steps of:
providing a wound retractor comprising a retracting member, and a proximal member;
inserting the retracting member into a wound opening;
locating the proximal member externally of the wound opening; and
moving the proximal member relative to the retracting member to shorten the axial extent of the retracting member to laterally retract the wound opening.

In one embodiment the retracting member comprises a proximal portion located proximally of the proximal member and a distal portion located distally of the proximal member, and the method comprises the step of decoupling the proximal portion from the distal portion after retraction of the wound opening.

The proximal portion may be decoupled from the distal portion by a cutting action.

In one arrangement the proximal member comprises an inner ring and an outer ring, and the method comprises the step of snap-fitting the inner ring relative to the outer ring to grip the retracting member therebetween. The inner ring may be snap-fitted relative to the outer ring after retraction of the wound opening.

In one embodiment the step of snap-fitting the inner ring relative to the outer ring decouples the proximal portion of the retracting member from the distal portion.

In another aspect the method comprises the step of mounting the retracting member to an obturator, and the obturator is inserted into the wound opening to insert the retracting member into the wound opening.

Typically, the method comprises the step of sealing the retracted wound opening.

BRIEF DESCRIPTION OF THE DRAWINGS

The invention will be more clearly understood from the following description of some embodiments thereof, given by way of example only, with reference to the accompanying drawings, in which:

FIGS. 12 and 13 are cross-sectional, side views of a wound opening being retracted using the retractor of FIG. 1 and an obturator;

FIGS. 17 and 19 are perspective views of a distal end of other wound retractors according to the invention;

FIGS. 28 to 30 are views of a retractor distal ring;

FIGS. 34 and 35 are views of a further introducer tool;

DETAILED DESCRIPTION

Figure 1:
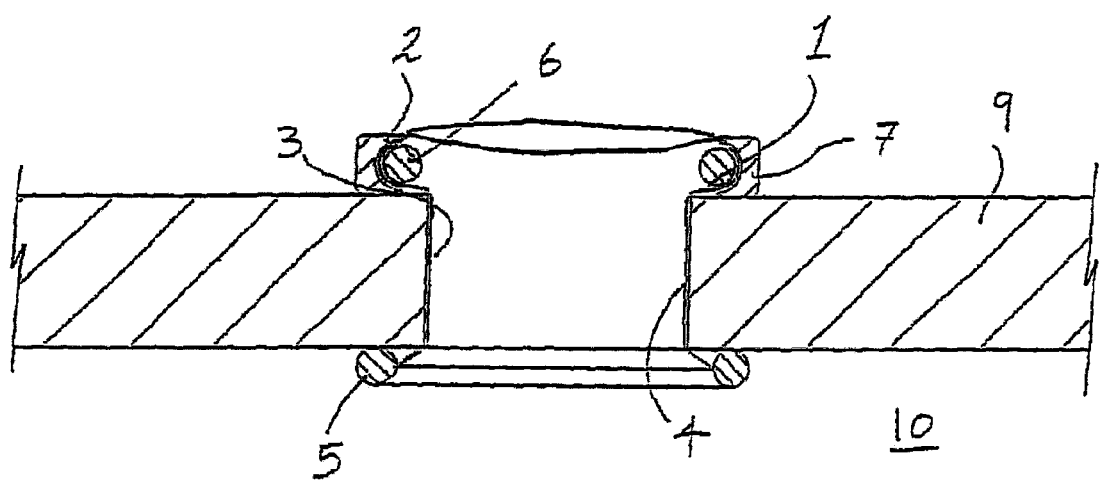
FIG. 1 is a cross-sectional, side view of a wound retractor according to the invention, in use.
Figure 2:
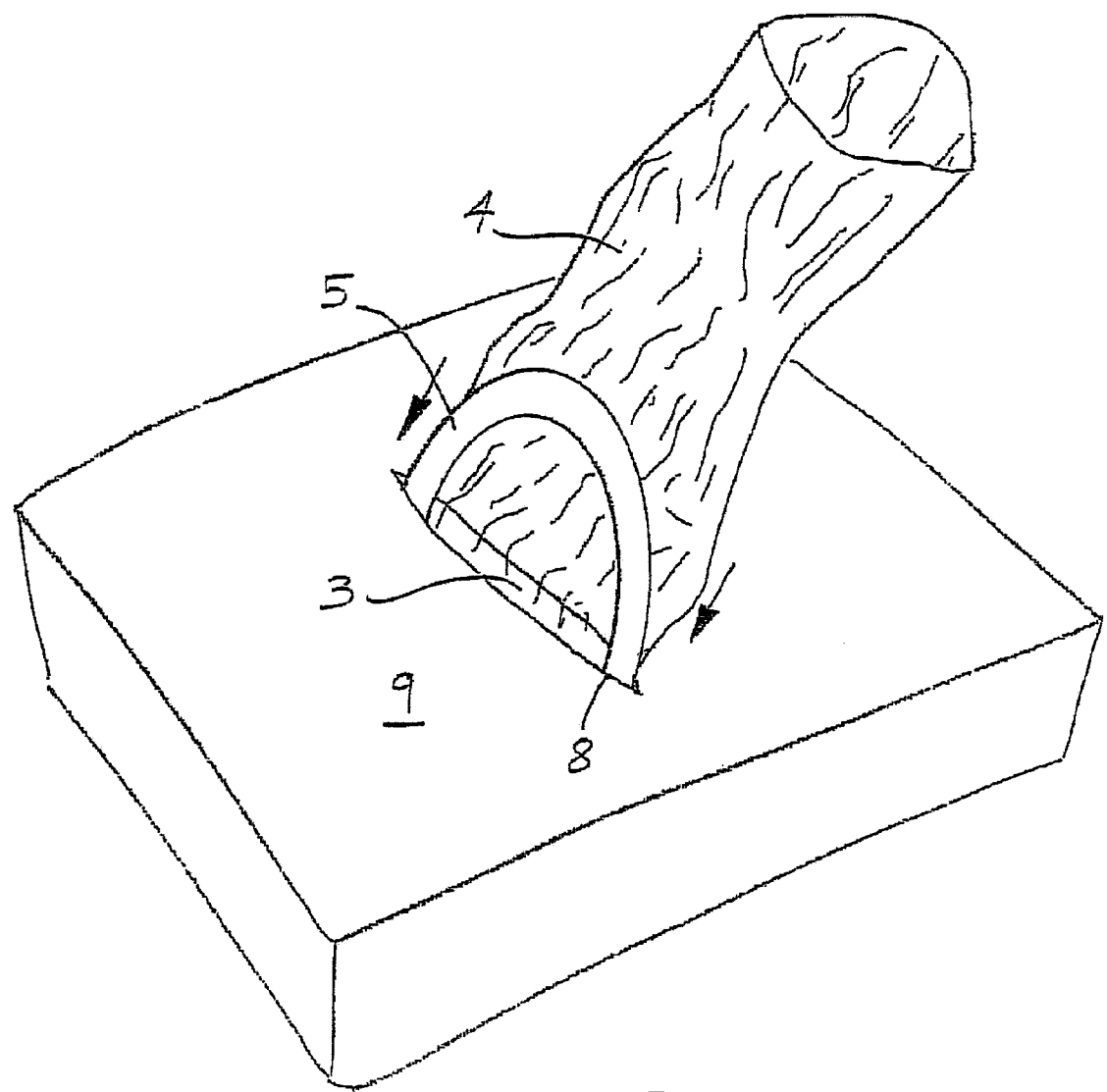
FIG. 2 is a perspective view of the retractor of FIG. 1 being inserted into a wound opening.

Referring to FIGS. 1 to 16, there is illustrated a wound retractor 1 comprising a proximal member 2 for location, in use, externally of a wound opening 3, a retracting member 4 for insertion into the wound opening 3, and a distal member 5 coupled to a distal end of the retracting member 4.

In this case, the retracting member 4 is provided in the form of a sleeve of flexible, polymeric film material which lines the sides of the wound opening 3 when the retractor 1 is in use (FIG. 1). The distal member 5 in this case comprises a resilient O-ring.

The proximal member 2 is provided, in this case, in the form of an annular ring means having an inner ring 6 and an outer ring 7 with the retracting member 4 lead between the rings 6, 7. The inner ring 6 has a circular cross-section and the outer ring 7 defines a "C"-shaped recess. In this manner a projecting portion of the inner ring 6 may be located in a snap-fit manner in the complimentary recess of the outer ring 7. The inner ring 6 is configured to be a relatively tight fit in the recess of the outer ring 7 to securely grip the retracting member 4 between the two rings 6, 7.

Figure 3:
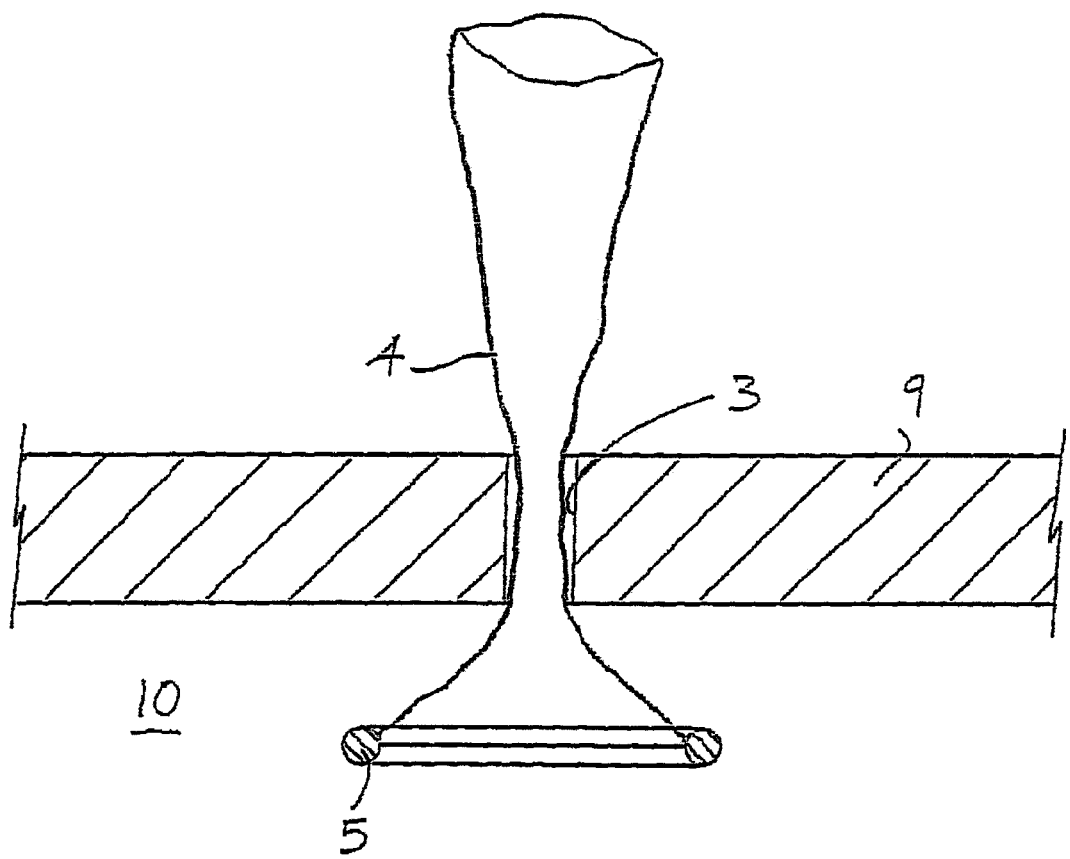
FIGS. 3 to 5, 7 and 9 are cross-sectional, side views of the wound opening being retracted using the retractor of FIG. 1
Figure 4:
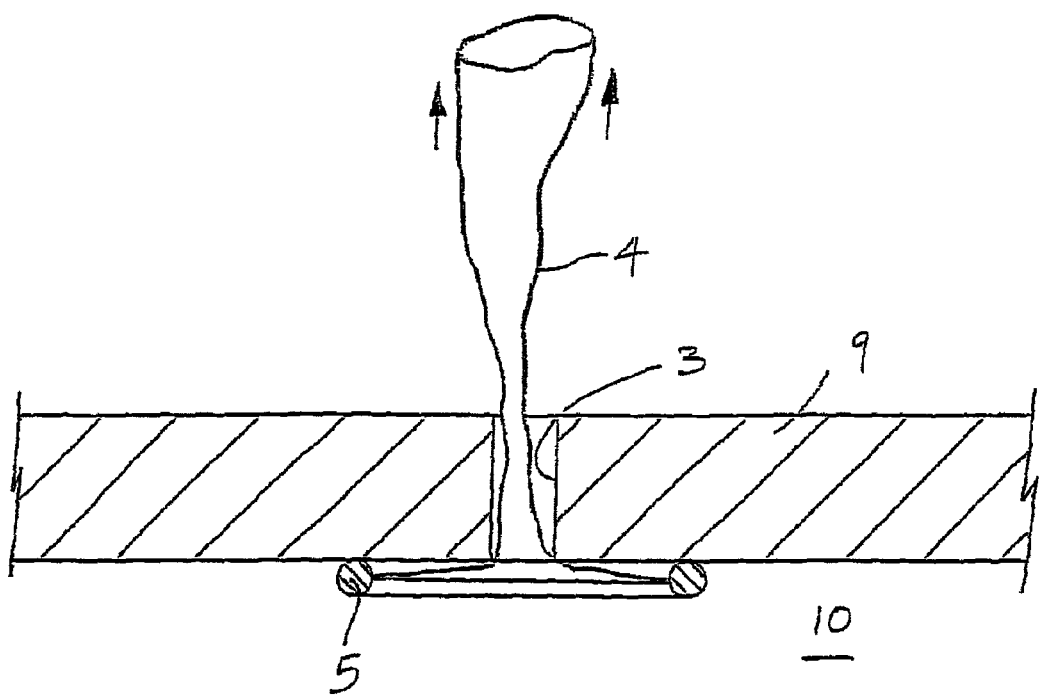

In use, a relatively small incision 8 is made in an abdominal wall 9 to form the wound opening 3. A typical length for the incision 8 to accommodate instruments and/or for specimen removal is from 3 to 35 millimetres. For an instrument, typically the incision is length will be in the range of 5 to 15 millimetres. The resilient distal O-ring 5 is then manipulated into an elongate, oblong shape by squeezing the distal O-ring 5 to facilitate insertion of the distal O-ring 5 through the wound opening 3 (FIG. 2), until the distal O-ring 5 is fully located within the abdominal cavity 10 and the sleeve 4 lines the wound opening 3 (FIG. 3). The sleeve 4 is then pulled upwardly to cause the distal O-ring 5 to engage with the internal surface of the abdominal wall 9 (FIG. 4).

Figure 5:
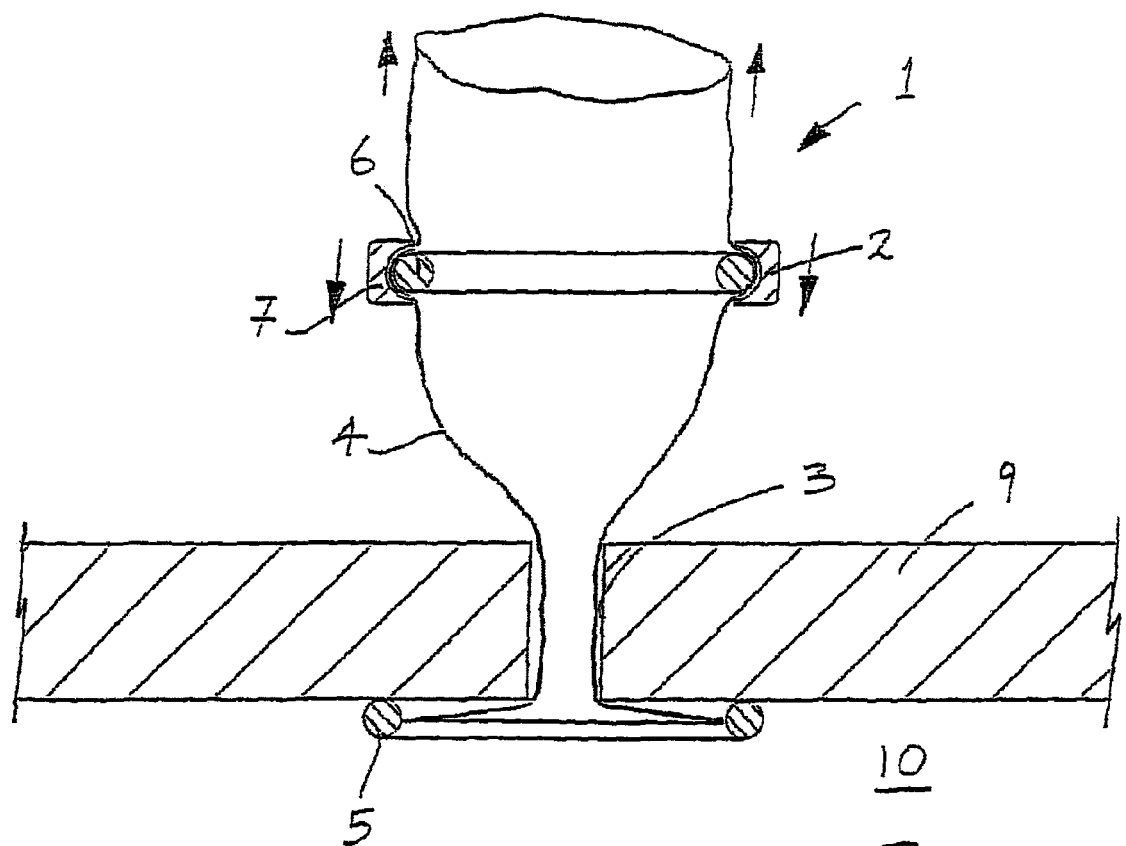
Figure 6:
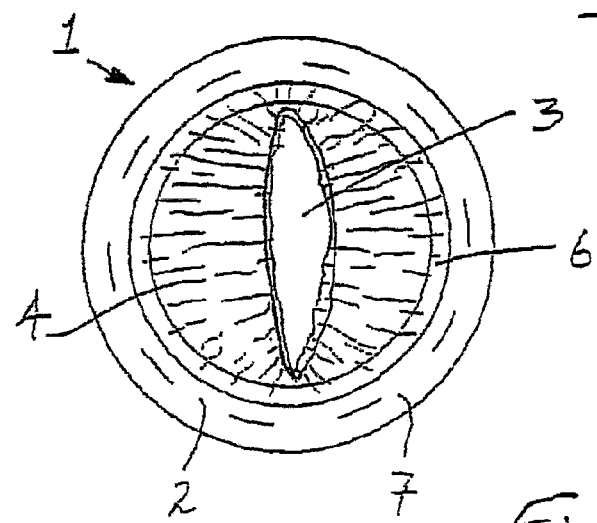
FIG. 6 is a plan view of the retractor and the wound opening of FIG. 5.
Figure 7:
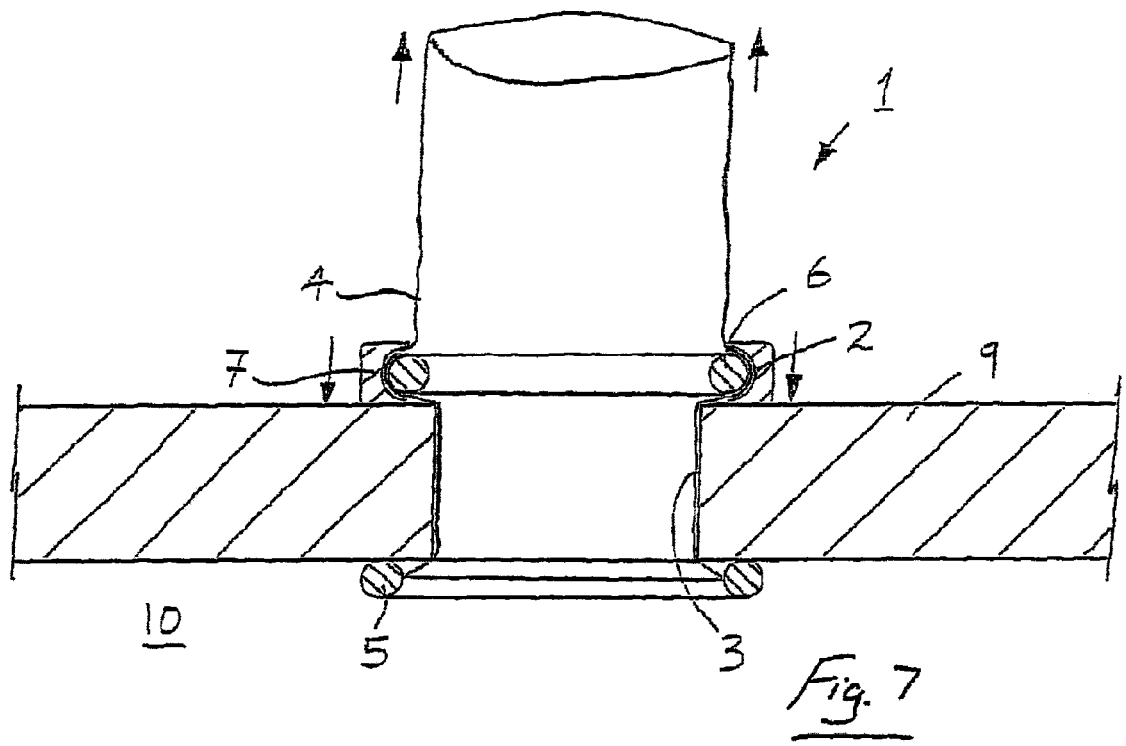
Figure 8:
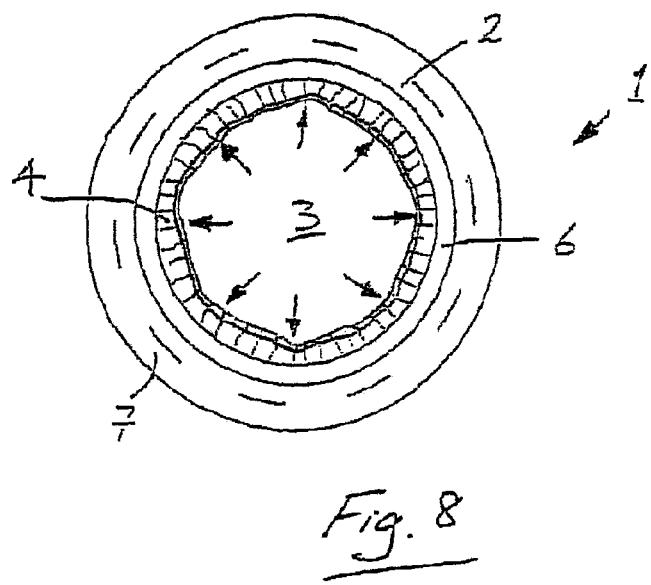
FIG. 8 is a plan view of the retractor and the wound opening of FIG. 7.

Next the proximal member 2 is threaded over the sleeve 4 with the sleeve 4 passing between the inner ring 6 and the outer ring 7. The proximal member 2 is then moved downwardly relative to the sleeve 4 by pulling the sleeve 4 taut upwardly and pushing the proximal member 2 downwardly (FIGS. 5 and 6). This action of moving the proximal member 2 relative to the sleeve 4 shortens the axial extent of the portion of the sleeve 4 which lines the wound opening 3, and thereby results in lateral retraction of the wound opening 3, as illustrated in FIGS. 7 and 8.

The tight-fit arrangement of the inner ring 6 in the recess of the outer ring 7 ensures that the sleeve 4 is securely gripped between the rings 6, 7. Thus the proximal member 2 acts as a lock to maintain the wound opening 3 in the retracted configuration illustrated in FIGS. 7 and 8.

Figure 9:
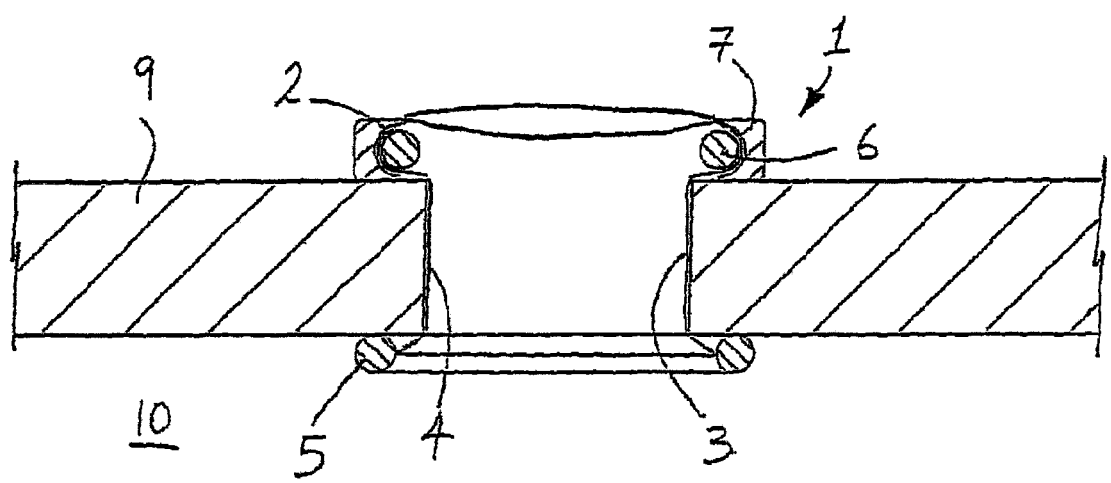

The portion of the sleeve 4 proximally of the rings 6, 7 is thereafter surplus to requirements and may be removed, for example by cutting it away (FIG. 9).

By engaging the internal surface of the abdominal wall 9, the distal O-ring 5 acts as an anchor to maintain the retractor 1 in position in the wound opening 3, during use.

Figure 10:
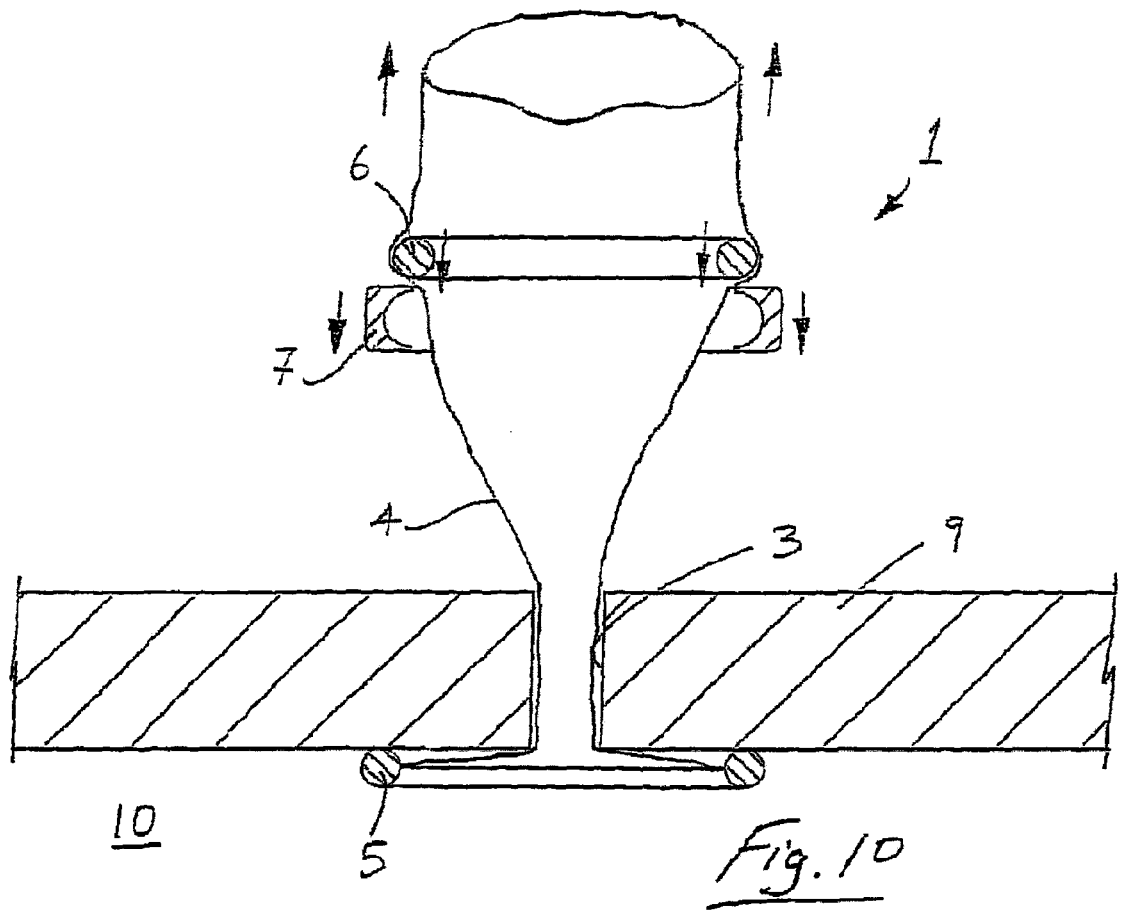
FIGS. 10 and 11 are views similar to FIGS. 5 and 6 of a wound opening being retracted in an alternative manner using the retractor of FIG. 1.
Figure 11:
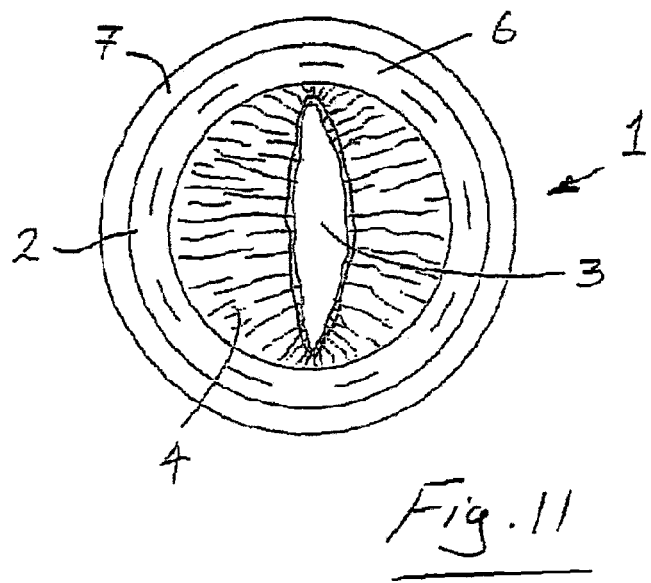

An alternative method of using the wound retractor 1 to retract the wound opening 3 is illustrated in FIGS. 10 and 11. In this case, the inner ring 6 and the outer ring 7 are moved downwardly relative to the sleeve 4 before the inner ring 6 is snap-fitted into position in the recess of the outer ring 7. The inner ring 6 is located above the outer ring 7.

The inner ring 6 is pushed downwardly, which causes the outer ring 7 to move downwardly also, while pulling the sleeve 4 taut upwardly until the outer ring 7 engages the external surface of the abdominal wall 9. Further pushing of the inner ring 6 downwardly then causes the inner ring 6 to snap into position in the recess of the outer ring 7 securely gripping the sleeve 4 between the rings 6, 7. The action of the inner ring 6 snapping into position in the recess of the outer ring 7 may be configured to cut the sleeve 4 for subsequent removal of the surplus proximal portion of the sleeve 4.

Referring to FIGS. 12 to 15 there is illustrated another method of using the wound retractor 1. In this case the retractor 1 is mounted to a blunt obturator 11 before insertion into the wound opening 3. The obturator 11 and the retractor 1 are then inserted together through the wound opening 3 until the distal O-ring 5 is fully located within the abdominal cavity 10 and the sleeve 4 lines the wound opening 3 (FIG. 12).

The distal O-ring 5 is engaged with the internal surface of the abdominal wall 9, and the proximal member 2 is moved downwardly relative to the sleeve 4 (FIG. 13), in a manner similar to that described previously with reference to FIGS. 4 to 8. The obturator 11 may then be removed from the wound opening 3. The proximal member 2 acts as a lock thereafter to maintain the wound opening 3 in the retracted configuration.

It has been found that the use of the obturator 11 may assist in deployment of the wound retractor 1. In particular, retraction of the wound opening 3 by means of the sleeve 4 during the set-up procedure is not required when the obturator 11 is employed.

A sharp obturator could alternatively be employed in a similar manner to that described previously with reference to FIGS. 12 and 13. A sharp obturator has the additional advantage that the initial incision 8 in the abdominal wall 9 could be made using the sharp obturator.

Figure 15:
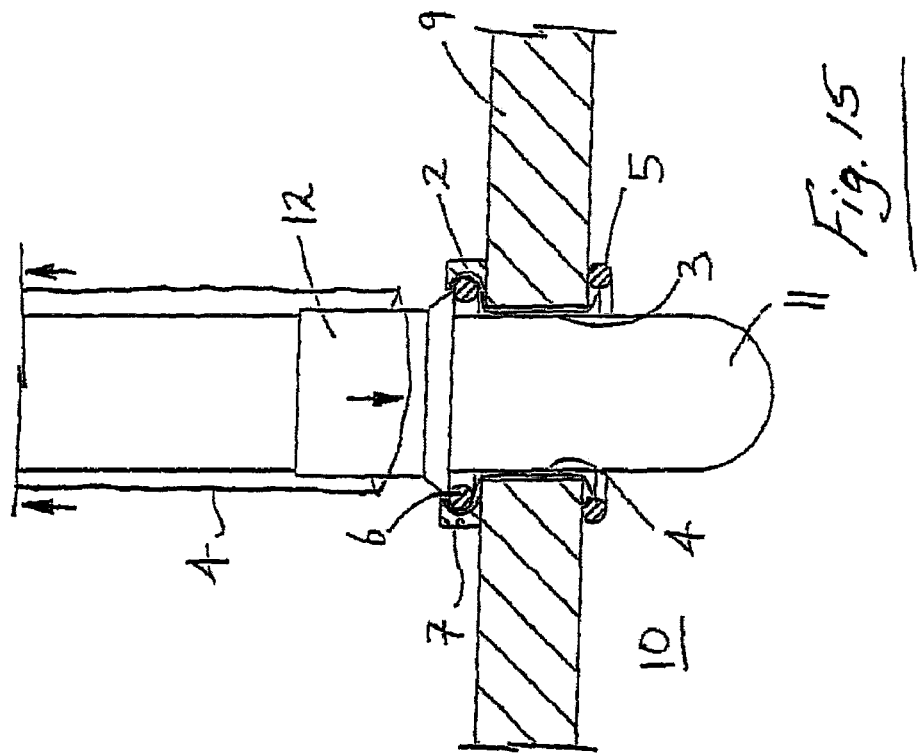
FIGS. 14 and 15 are cross-sectional, side views of a wound opening being retracted using the retractor and the obturator of FIGS. 12 and 13 and a pusher.
Figure 14:
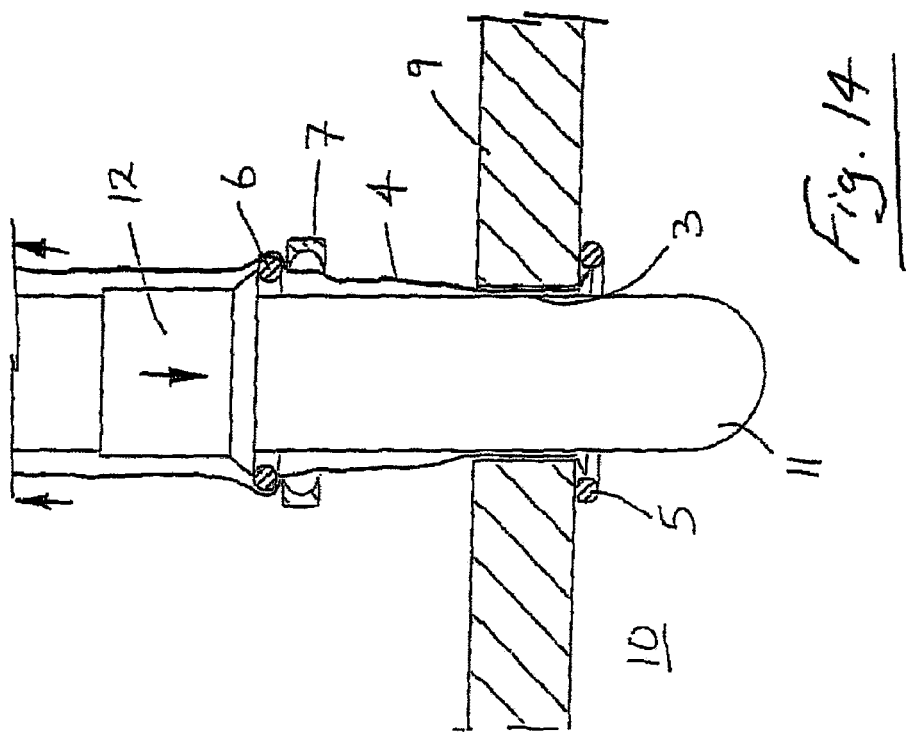

FIGS. 14 and 15 illustrate a further method of retracting the wound opening 3 using the wound retractor 1, which is similar to the method described previously with reference to FIGS. 12 and 13.

In this case, the retractor 1 is mounted to the obturator 11 before the inner ring 6 is snap-fitted into position in the recess of the outer ring 7. A tubular pusher 12 is slidably mounted around the obturator 11 for engagement with the inner ring 6.

By pushing on the pusher 12 downwardly while pulling the sleeve 4 taut upwardly, the rings 6, 7 are moved downwardly until the outer ring 7 engages the external surface of the abdominal wall 9. Further pushing of the pusher 12 downwardly then causes the inner ring 6 to snap into position in the recess of the outer ring 7, and simultaneously causes cutting of the sleeve 4.

The sleeve 4 is thus securely gripped between the rings 6, 7 to maintain the wound opening 3 in the retracted configuration. Also the surplus proximal portion of the sleeve 4 which has been cut away may be removed.

Figure 16:
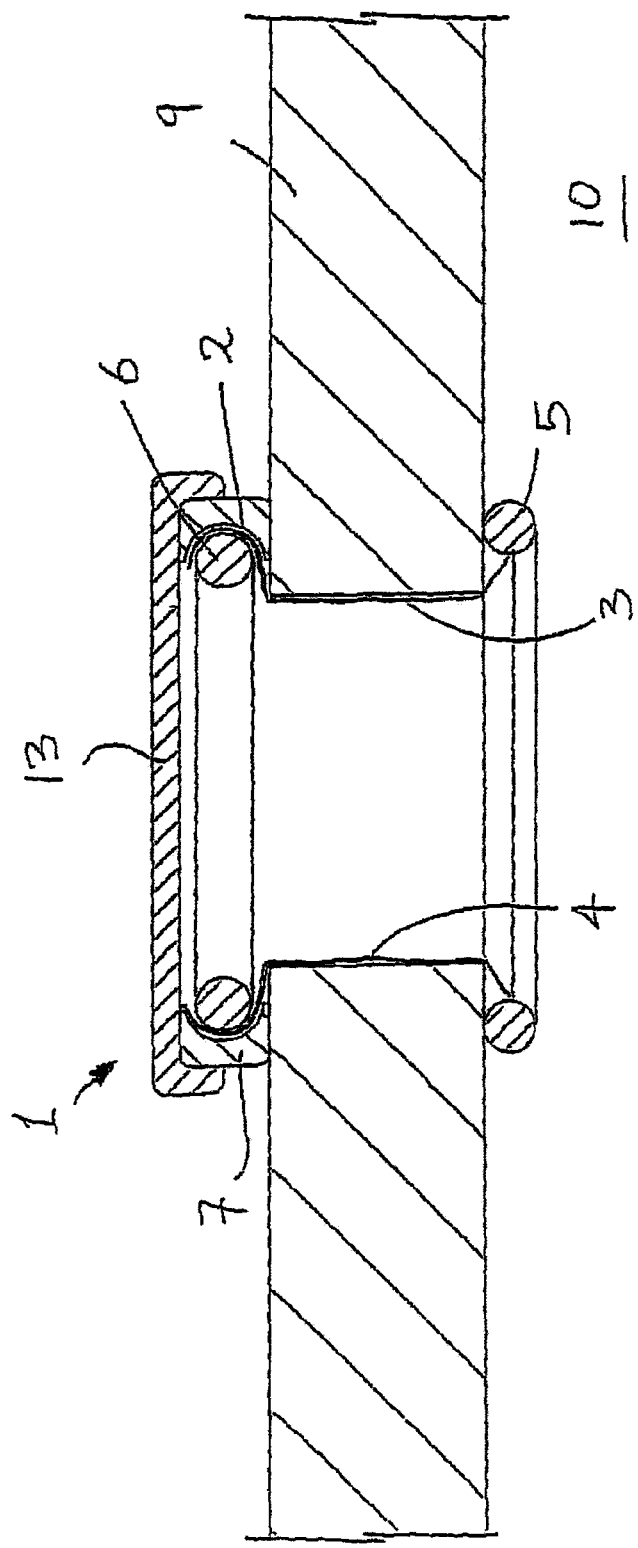
FIG. 16 is a cross-sectional, side view of the retractor of FIG. 1 and a sealing cap.

The wound opening 1 may include means to seal the retracted wound opening 3. For example, FIG. 16 illustrates a sealing cap 13 releasably mounted to the proximal member 2 externally of the wound opening 3. The cap 13 may be temporarily mounted to the proximal member 2 to maintain a gas-tight seal of the retracted wound opening 3, for example to maintain pneumoperitoneum within the abdominal cavity 10. If it is desired to access the abdominal cavity 10, and/or to remove matter from within the abdominal cavity 10, the cap 13 can be quickly and easily removed to reveal the retracted wound opening 3.

It will be appreciated that various other sealing means may alternatively be provided with the wound retractor 1. For example, one or more valves may be included to facilitate sealed access of an object, such as an instrument, through the retracted wound opening 3.

The distal end of the sleeve 4 may be flared distally outwardly towards the distal O-ring 20, as illustrated in the wound retractor 25 of FIG. 17. This arrangement enhances the anchoring of the retractor 25 in position in the wound opening 3 with less risk of the distal O-ring 20 being pulled up through the wound opening 3, during use.

A variety of different configurations are possible for the distal member of the wound retractor within the scope of this invention. For example, the distal member may be a standard O-ring 21, as illustrated in the wound retractor 26 of FIG. 18, or the distal member may be provided in the form of a flexible, annular disc 22, as illustrated in the wound retractor 27 of FIG. 19. It has been found that the disc 22 provides enhanced anchoring of the retractor 27 in position in the wound opening 3, during use.

Figure 22:
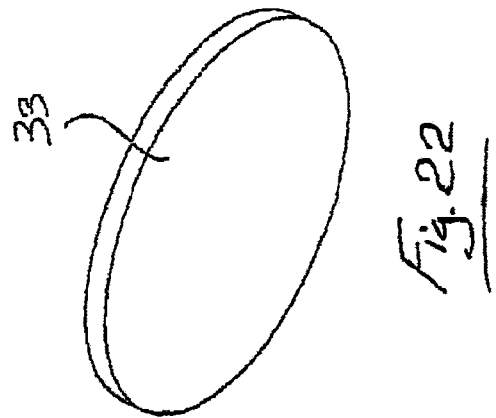
FIGS. 20 to 22 are perspective views of an inner ring part of other wound retractors according to the invention.
Figure 21:
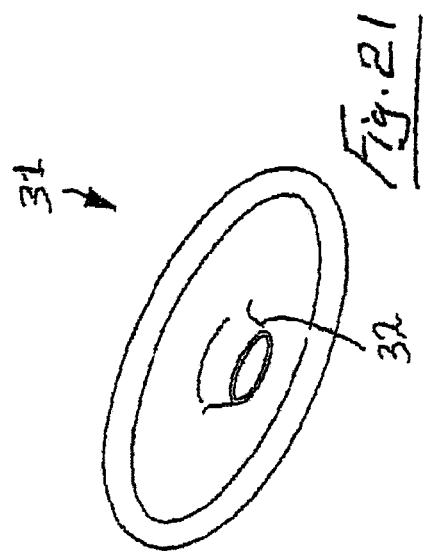
Figure 20:
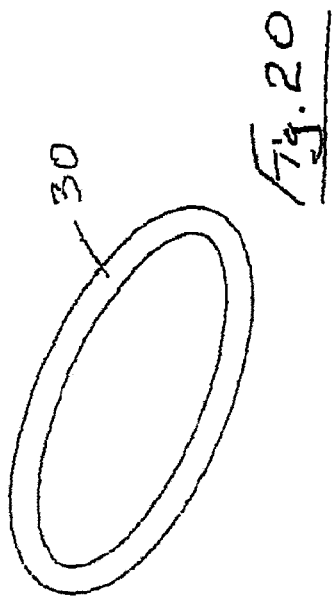

In addition, a variety of different configurations are possible for the proximal member of the wound retractor within the scope of the invention. For example, the inner ring of the proximal member may be provided in the form of a standard O-ring 30, as illustrated in FIG. 20. Alternatively one or more valves, such as a lip seal 32, may be provided as part of the inner ring 31, as illustrated in FIG. 21 to facilitate sealed access of an object, such as an instrument, through the proximal member. As a further alternative, the proximal member may comprise a closed cap 33 (FIG. 22) to completely seal the retracted wound opening 3, for example, to maintain pneumoperitoneum in the abdominal cavity 10.

Figure 23:
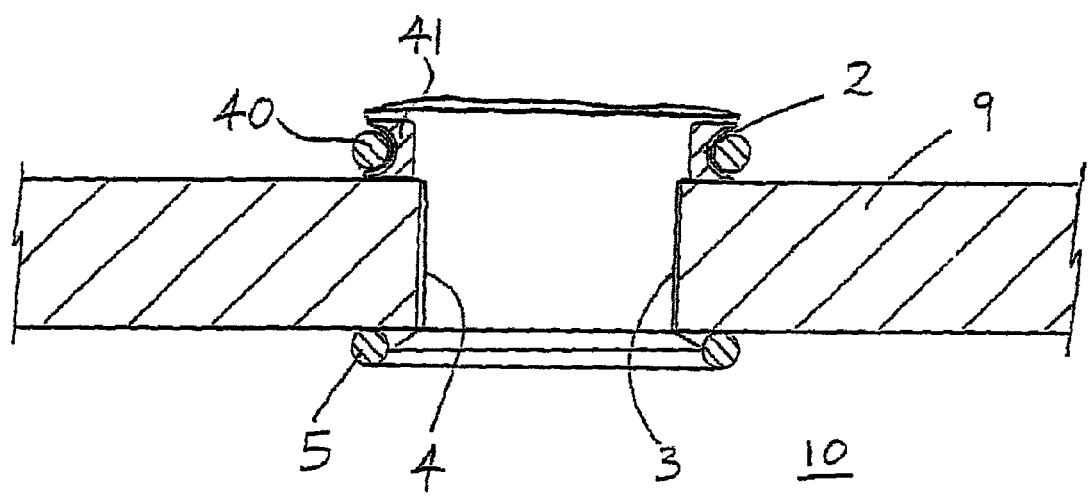
FIG. 23 is a cross-sectional, side view of another wound retractor according to the invention.

It will be appreciated that the configuration of the proximal member 2 may be reversed. For example, an inner ring 41 may define a "C"-shaped recess and an outer ring 40 may have a circular cross-section, as illustrated in FIG. 23.

Figure 24:
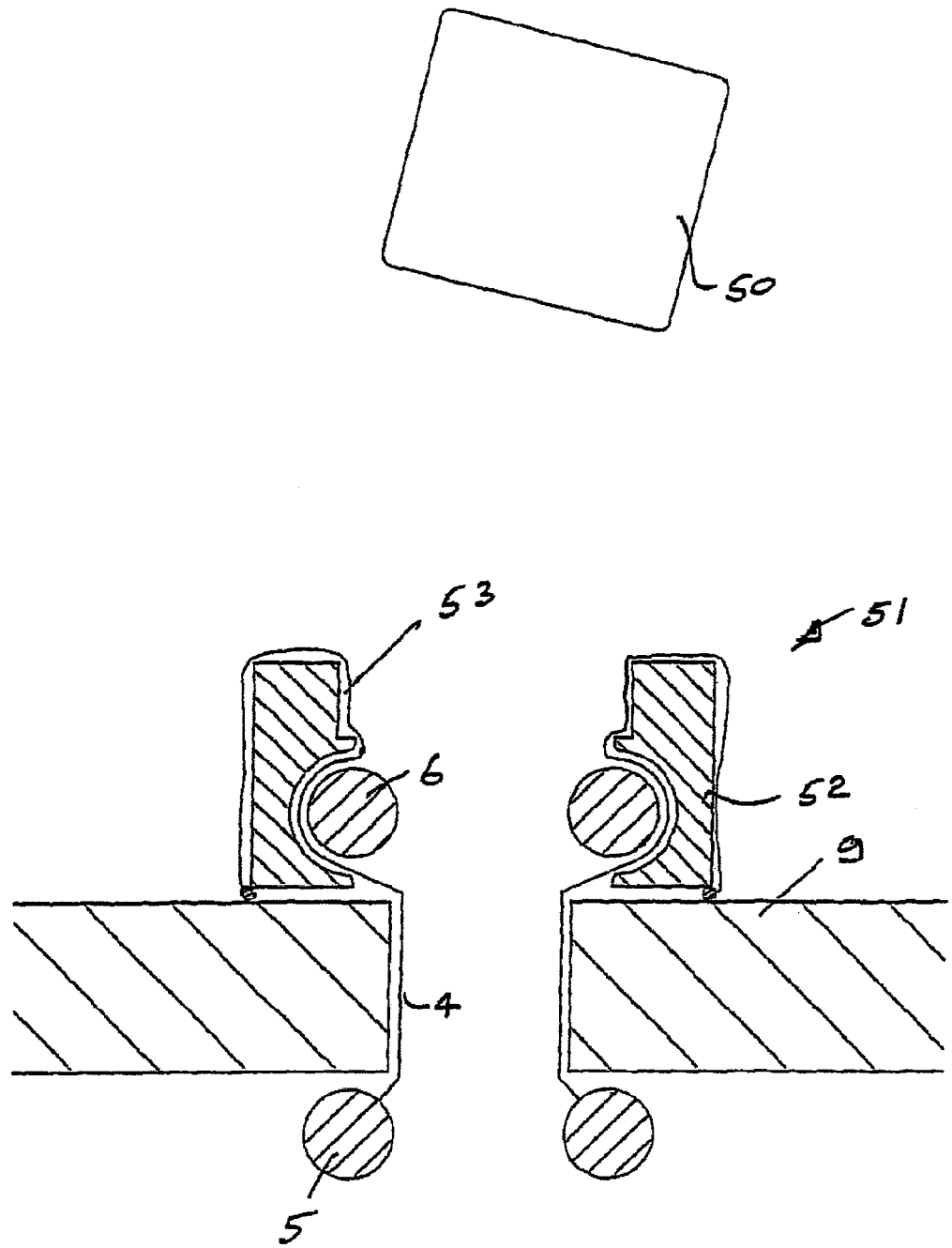
FIGS. 24 to 26 are cross sectional views of a retractor system.
Figure 25:
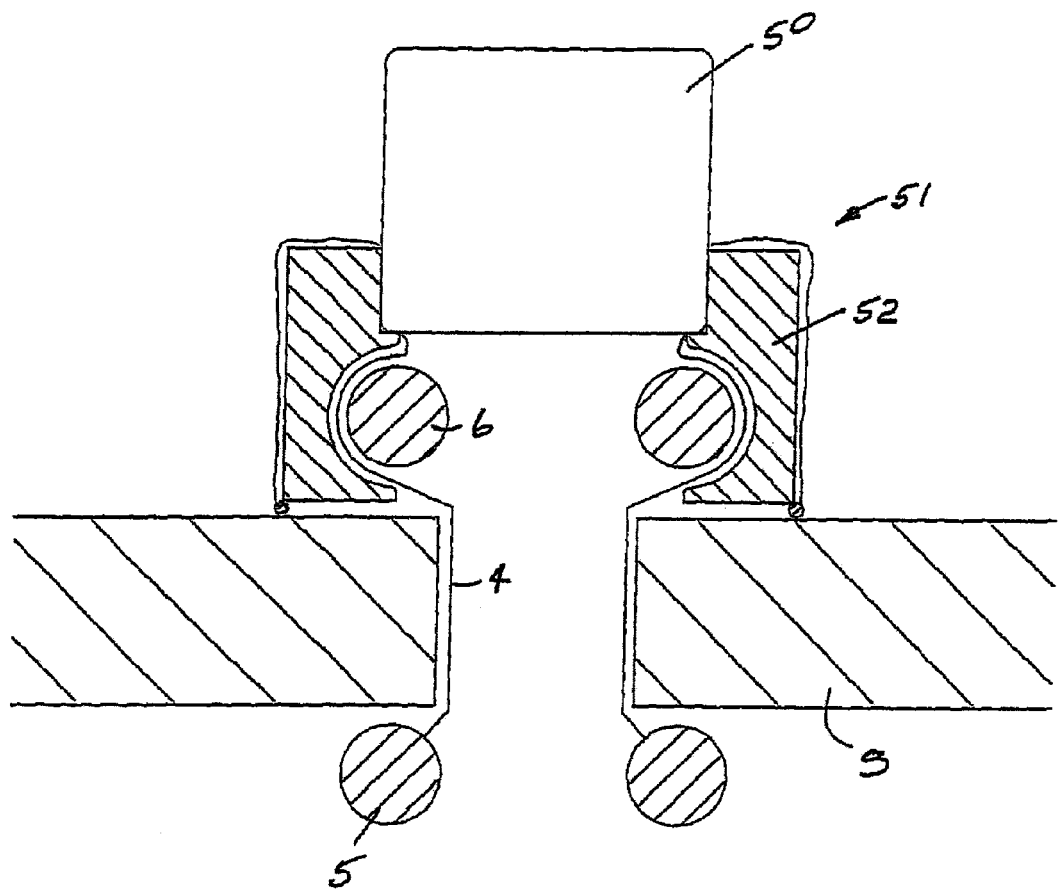
Figure 26:
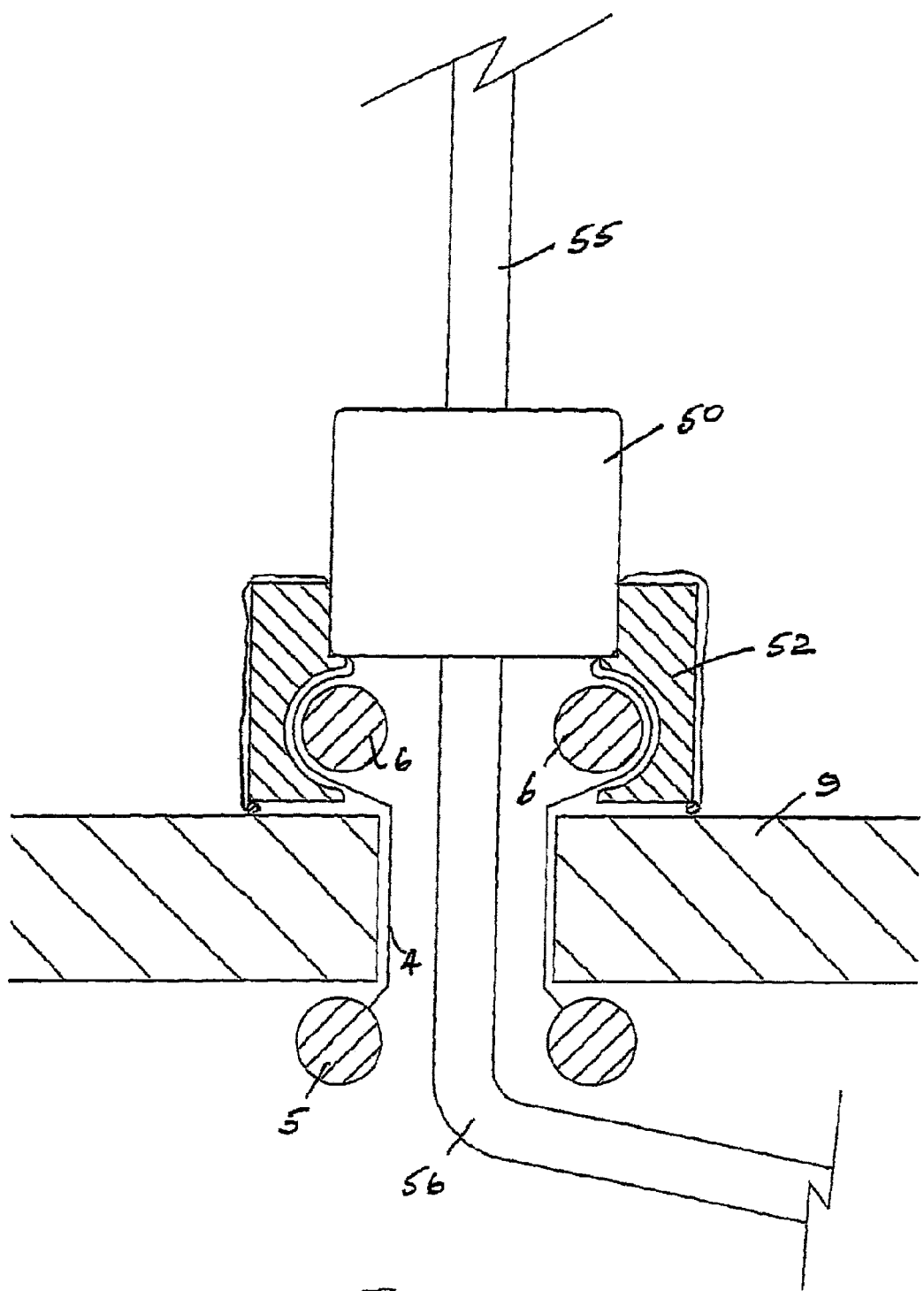

Referring now to FIGS. 24 to 26 another modular system is illustrated in which a valve 50 is releasably mounted to a retractor 51. The retractor 51 may be similar to the retractors described above, like parts being assigned the same reference numerals. The retractor 51 may have a proximal ring member 52 with a recess 53 to receive the valve 50. The sleeve 4 may be hooked over the proximal ring member 52, as illustrated. An instrument shaft 55 can readily pass through the valve 50 and the retractor 51. At least a section 56 of the shaft 55 can be bent or steered almost immediately distal of the retractor 51.

The access ports of the invention provide controlled radial expansion. Greater access is achieved using smaller incision. The incision size can be varied as required, for example for a laparoscopic procedure.

The retractor ensures that there is substantially no gas leakage from the wound margins and that it cannot be inadvertently pulled out of the incision The retractor can be used to seal any incision and without the requirement of a secondary sealing method such as suturing.

The retractor has minimum intra-abdominal profile. There is more working space in the abdomen which may be very important for some procedures such as pelvic surgery. The retractor also provides perineal access for operations such as radical prostatectomy.

The retractor also protects a wound from infection and cancer seeding. Upon removal, all areas of potential contamination are isolated from the incision.

The retractor also provides reduced extra-abdominal profile. This increases the effective working length of an instrument and provides a greater working area outside the abdomen.

The retractor will also increase the freedom of movement of conventional laparoscopic instruments during procedures.

Figure 27:
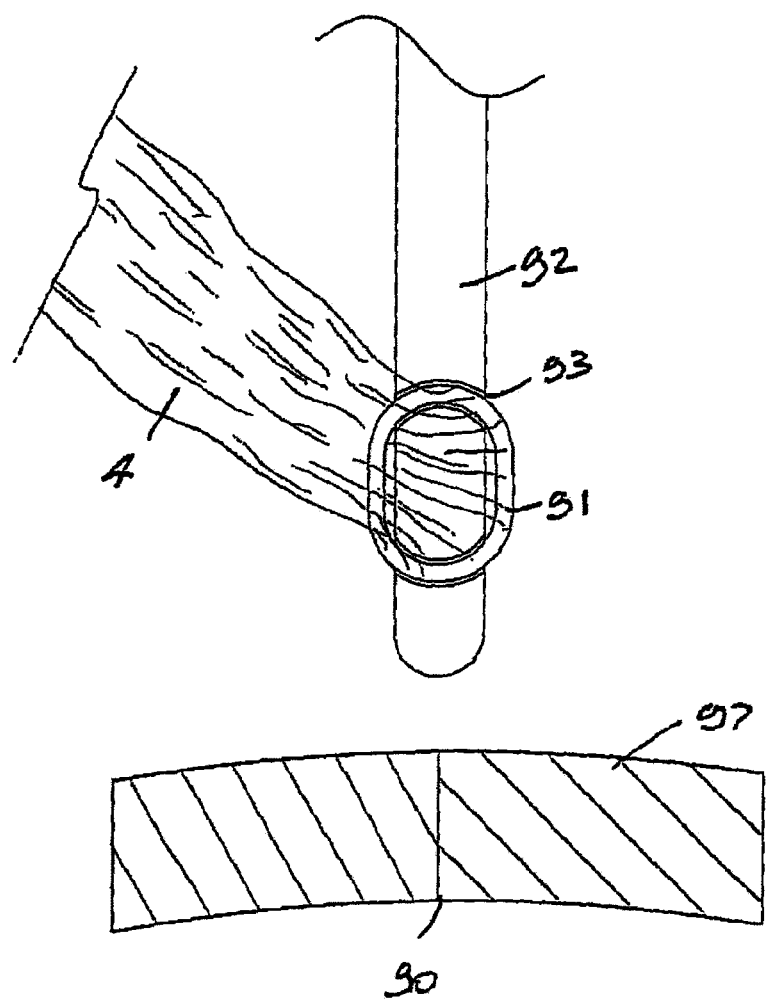
FIG. 27 is a view of an introducer tool according to the invention.

The retractor may be inserted through the abdominal wall as described below. An initial small incision 90 which is in the range 3 mm to 35 mm may be made in the abdominal wall 97 and an inner distal ring 91 of the retractor may be attached to an insertion tool 92 as illustrated in FIG. 27. The ring 91 is flexible and can be stretched or bent as illustrated for ease of insertion through the incision 90. The ring 91 may be retained in the stretched/bent insertion configuration using locating grooves 93 in the insertion tool 92. Alternatively or additionally as illustrated in FIGS. 28 to 30 the ring 91 may be split into a number (in this case 4) of sections 95 with an inner thread 96 passing between and linking the sections 95. The ring 91 can be bent as illustrated to reduce the profile in the insertion configuration. The system is biased so that the ring 91 re-forms into the circular configuration once released on insertion.

Figure 31:
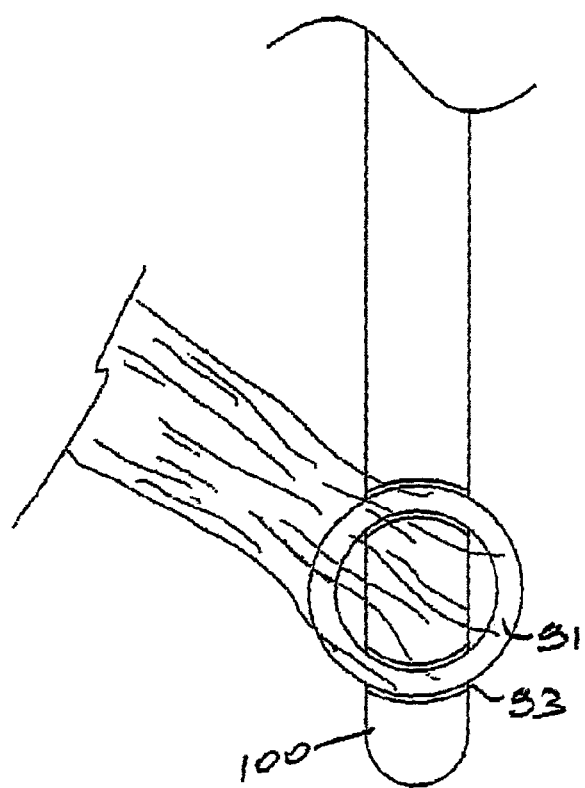
FIGS. 31 to 33 are views of another introducer tool.
Figure 32:
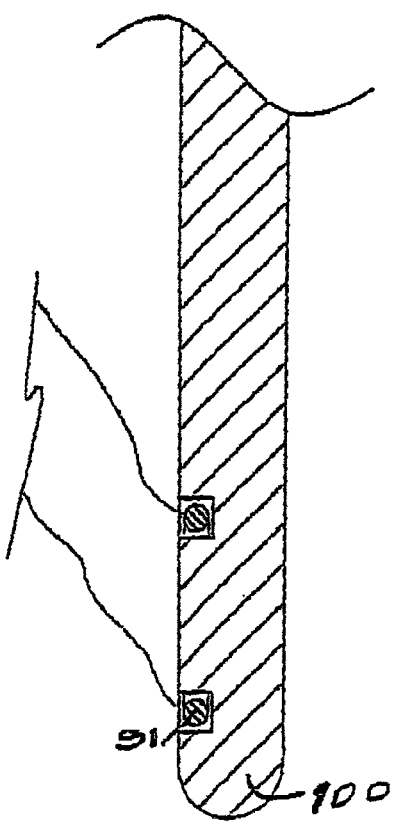
Figure 33:
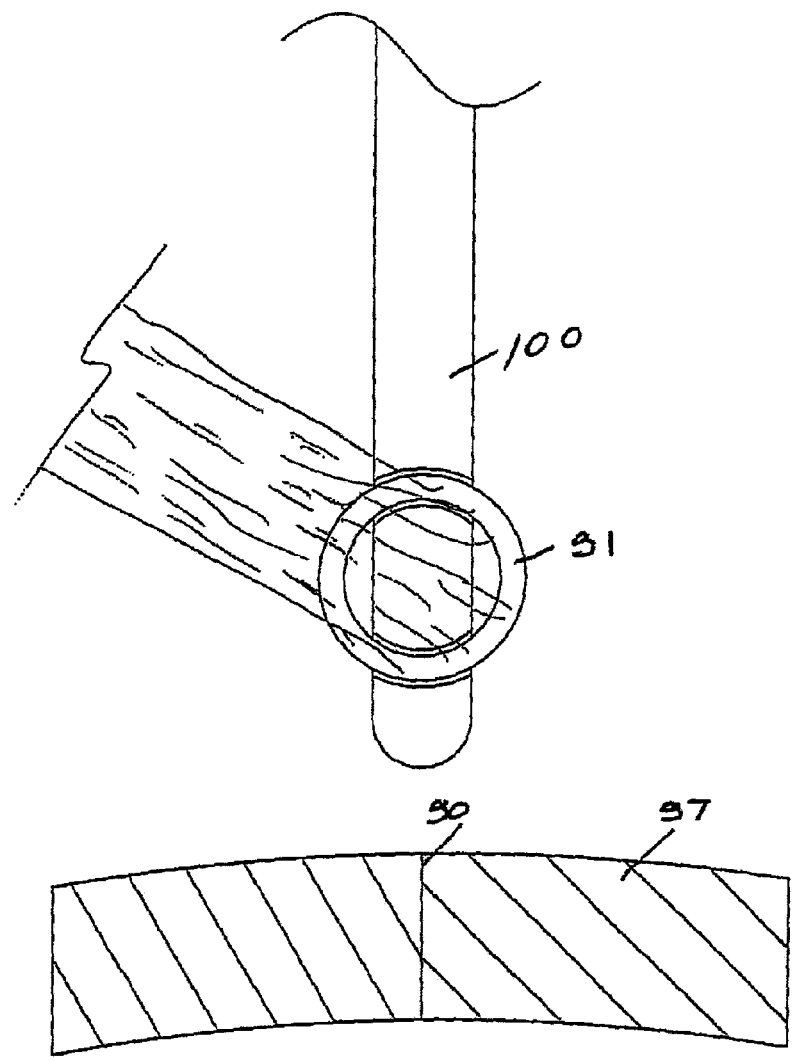
Figure 36:
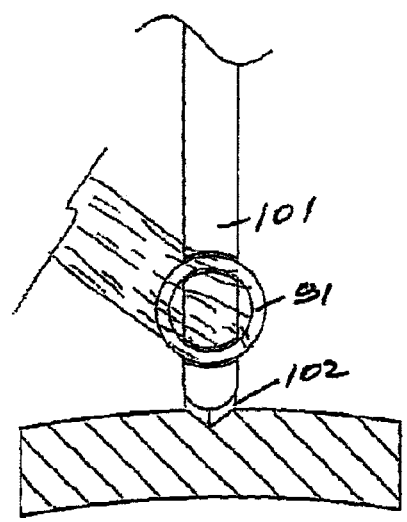
FIGS. 36 to 40 are cross sectional views of the tool of FIGS. 34 and 35, in use.
Figure 37:
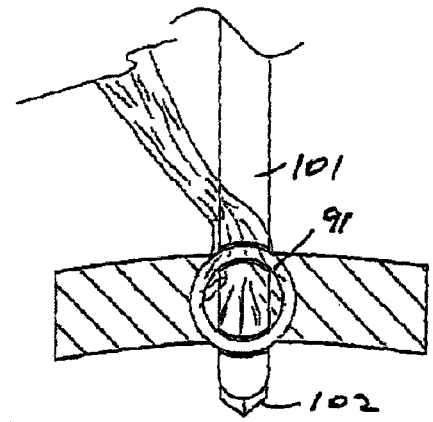
Figure 38:
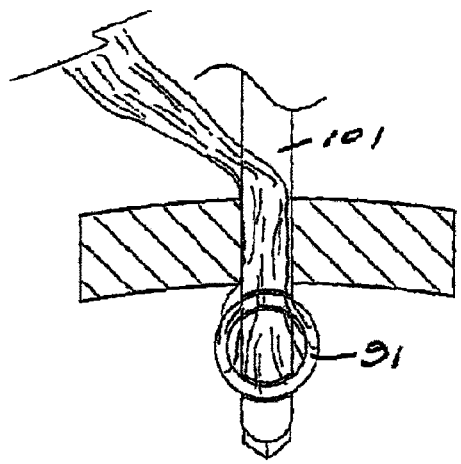
Figure 39:
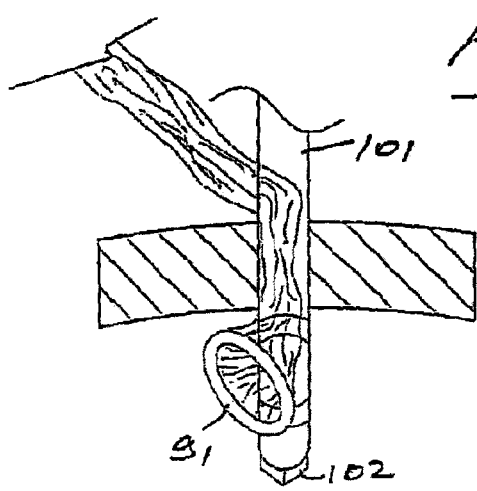
Figure 40:
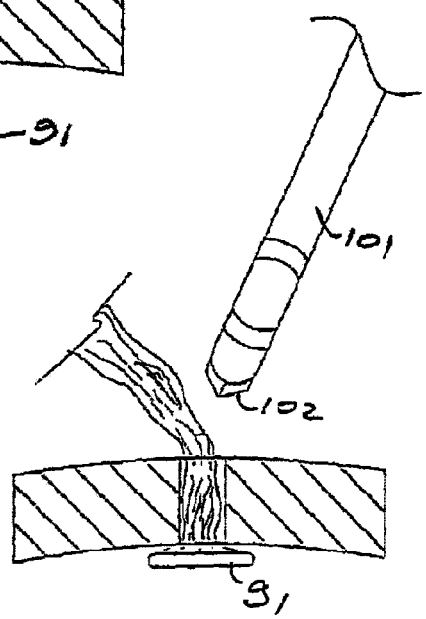

In some cases (FIGS. 31 to 33) the ring 91 may be inserted through the incision using a blunted or round-nosed obturator tool 100.

Alternatively as illustrated in FIGS. 34 and 35 the ring 91 may be inserted using an obturator/trocar tool 101 with a leading cutting blade 102. In this case, as illustrated in FIGS. 36 to 40, the tool 101 itself makes an incision in the abdominal wall, allowing the distal ring 91 of the retractor to be delivered and deployed, as illustrated.

Figure 42:
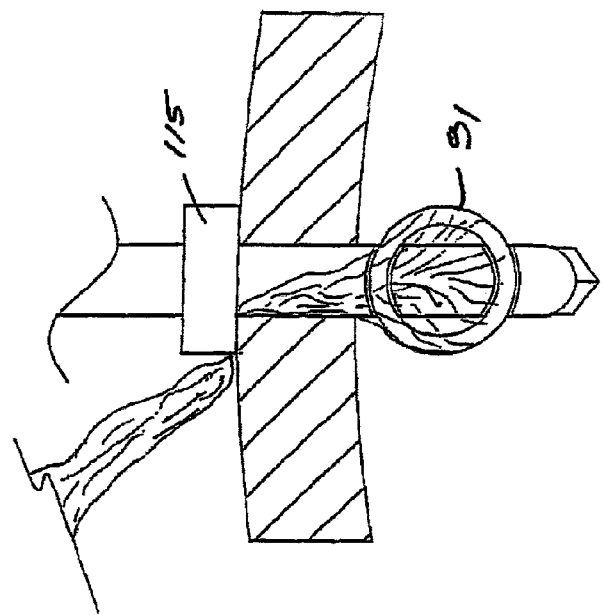
FIGS. 41 and 42 are cross sectional views of another introducer tool, in use.
Figure 41:
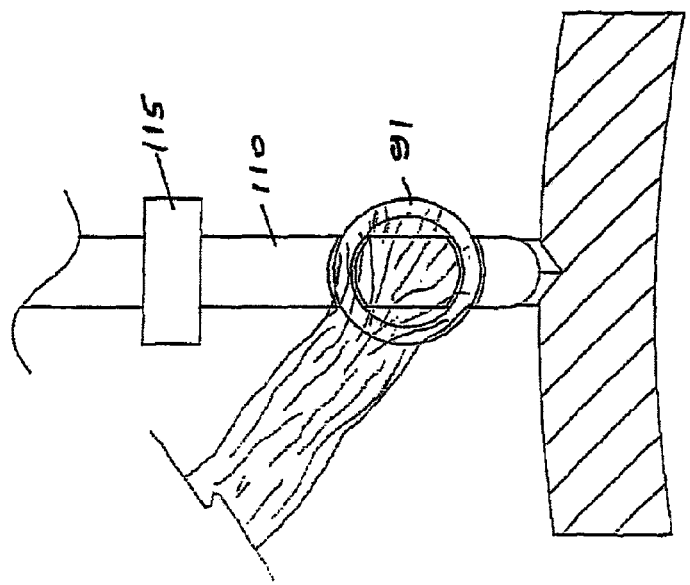
Figure 43:
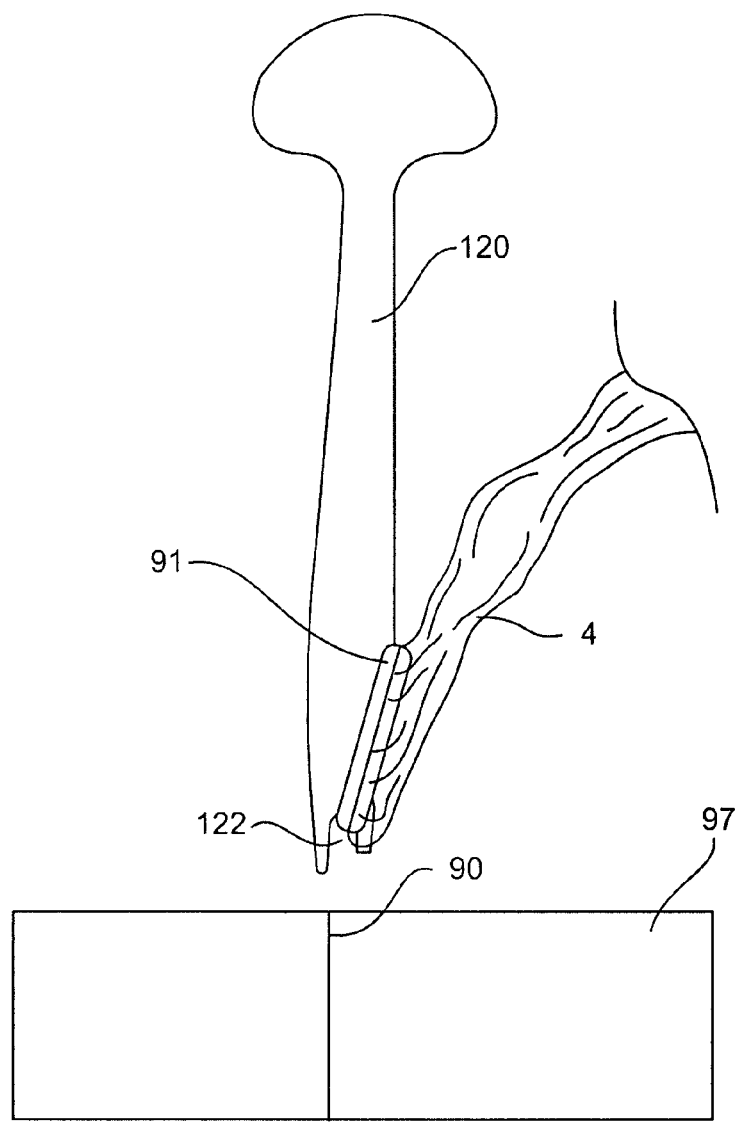
FIGS. 43 to 46 are cross sectional views of an introducer tool, in use.
Figure 44:
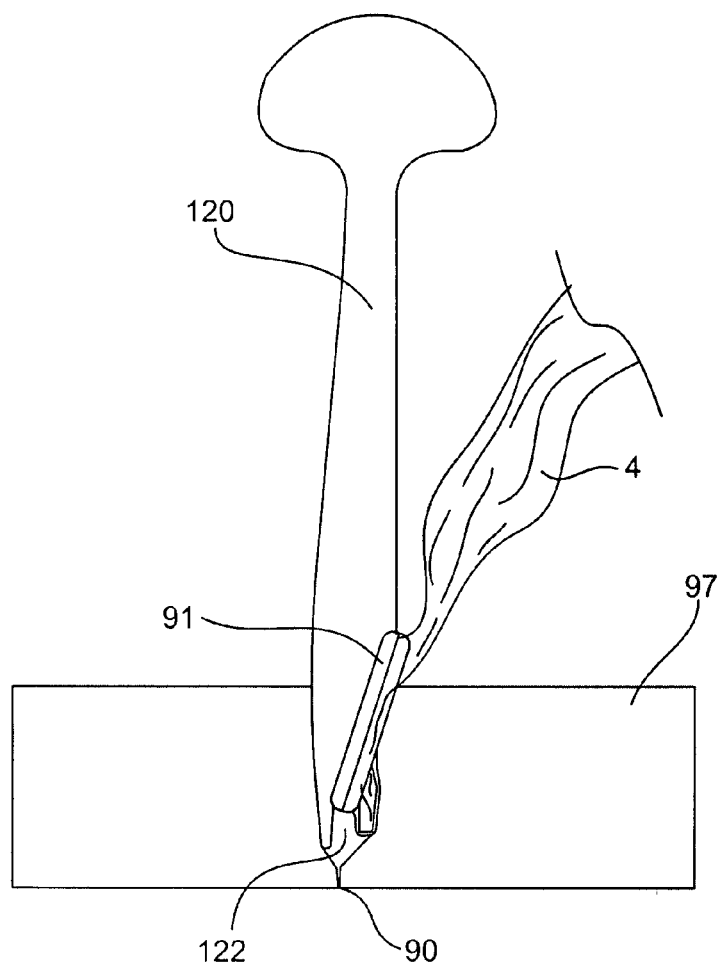
Figure 45:
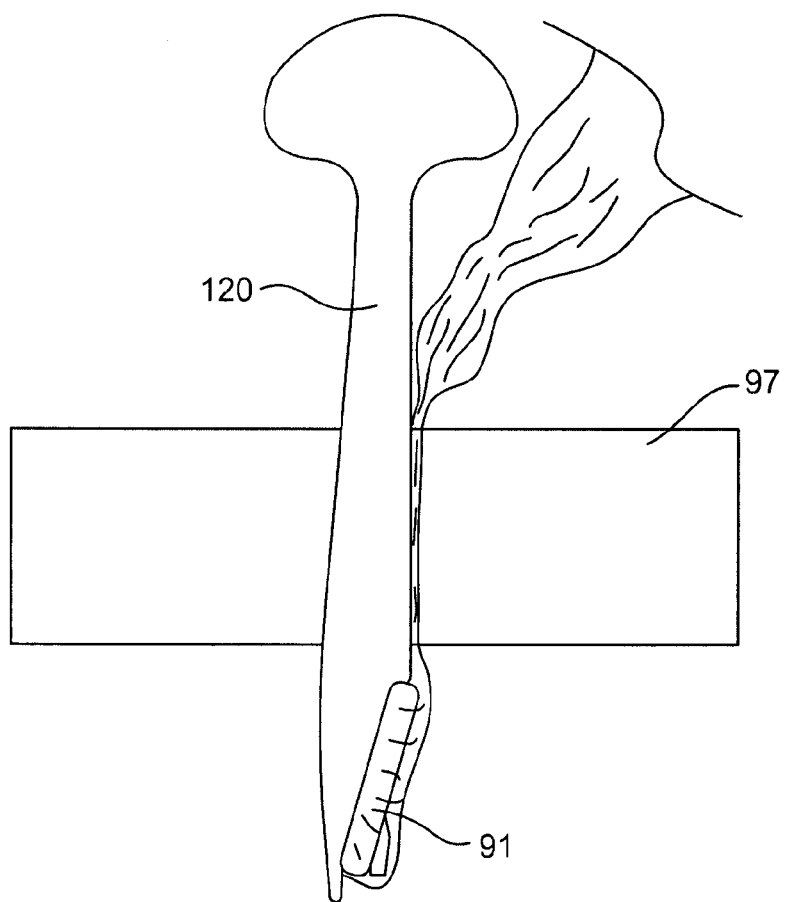
Figure 46:
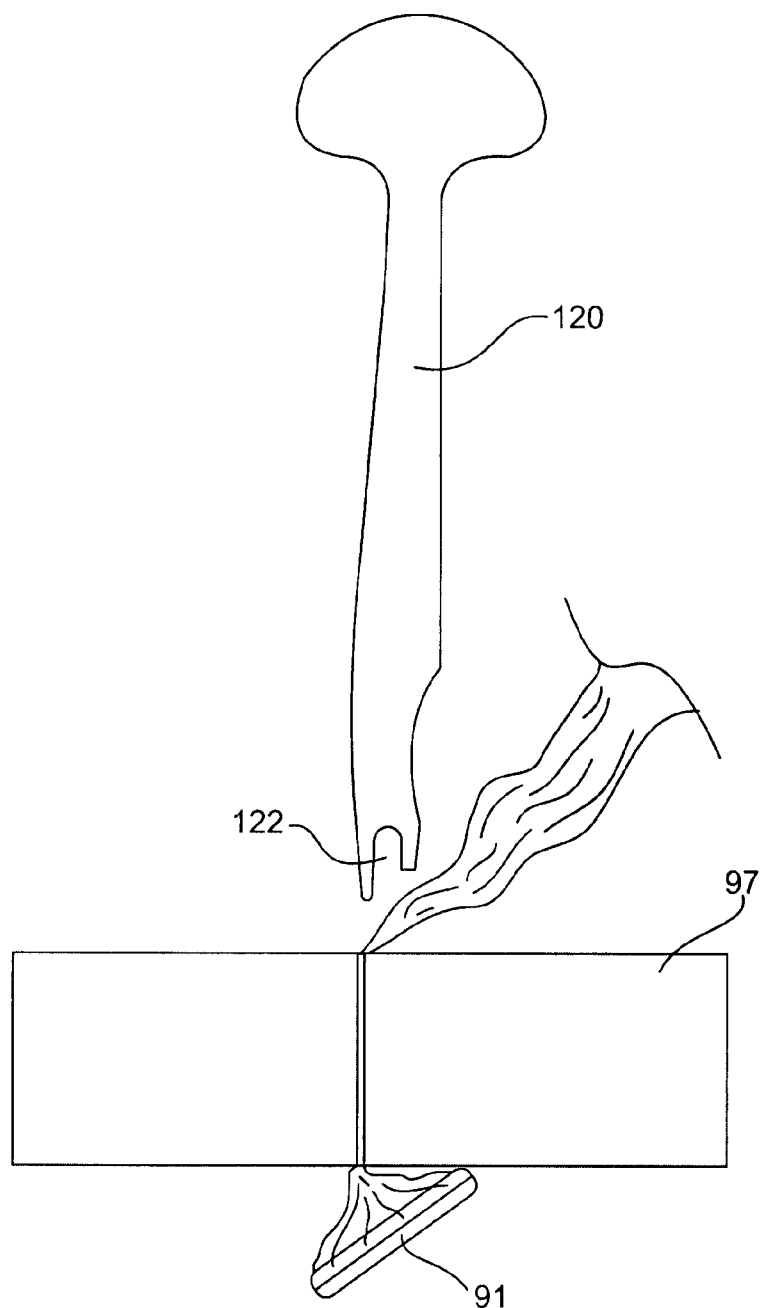
Figure 47:
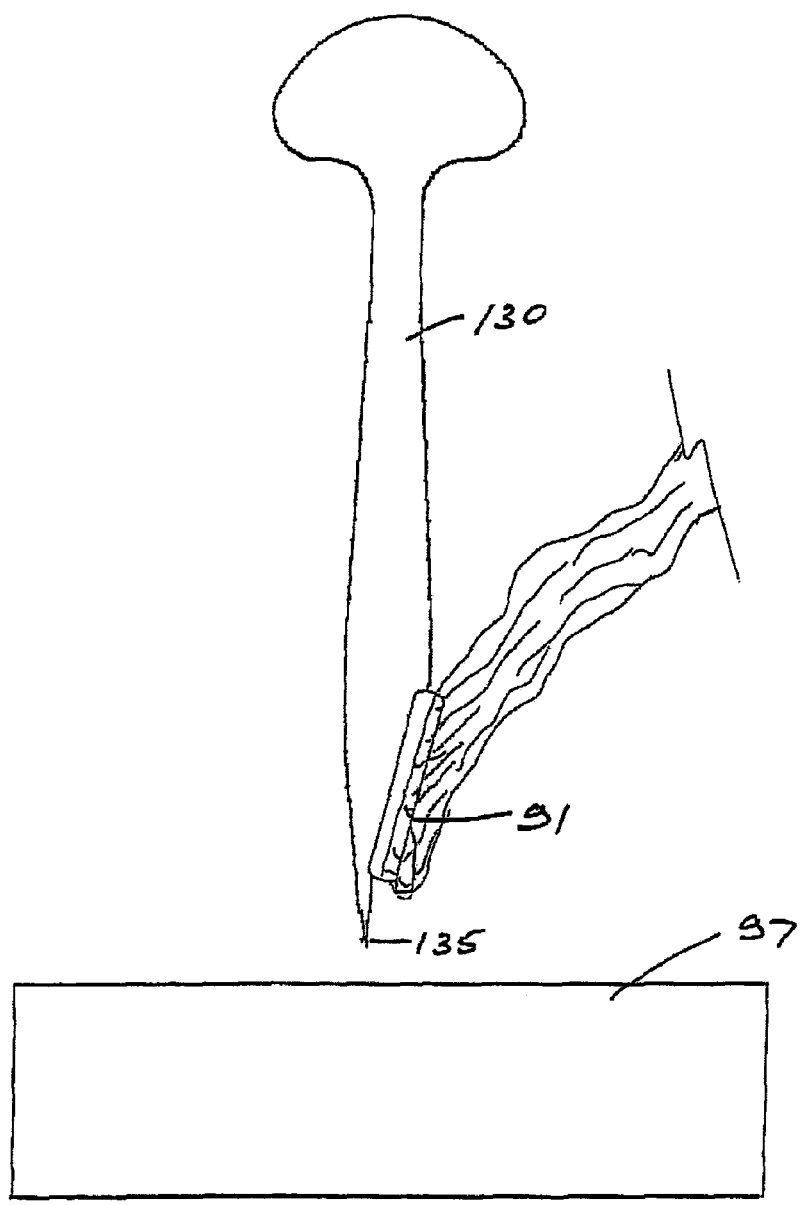
FIGS. 47 to 50 are cross sectional views of another introducer tool, in use.
Figure 48:
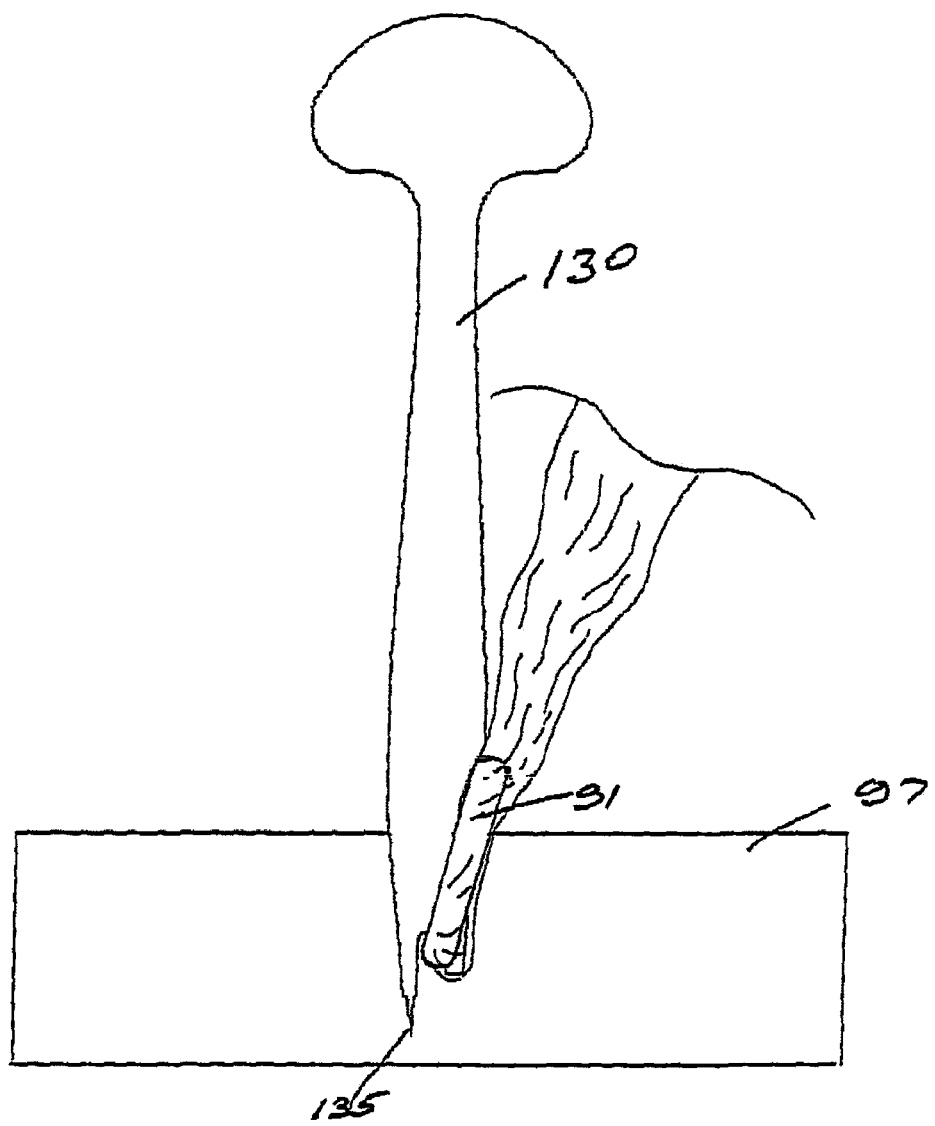
Figure 49:
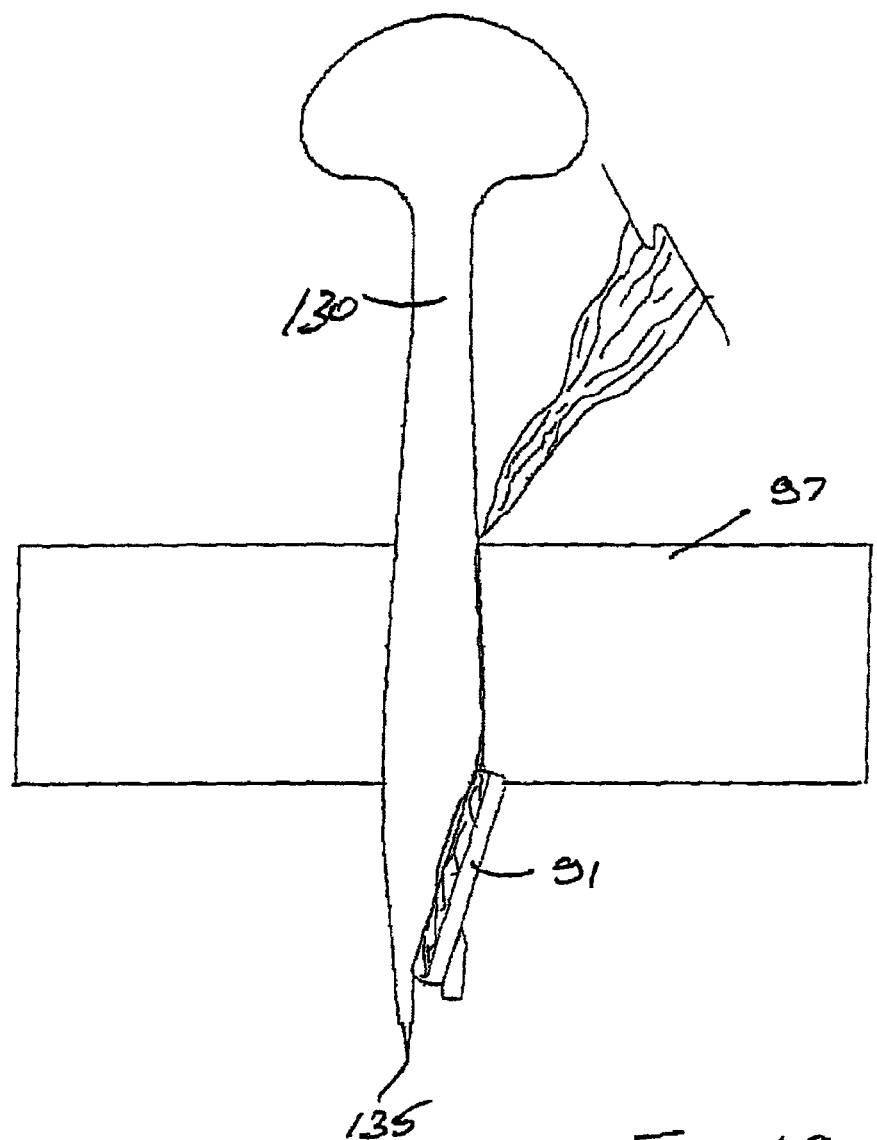
Figure 50:
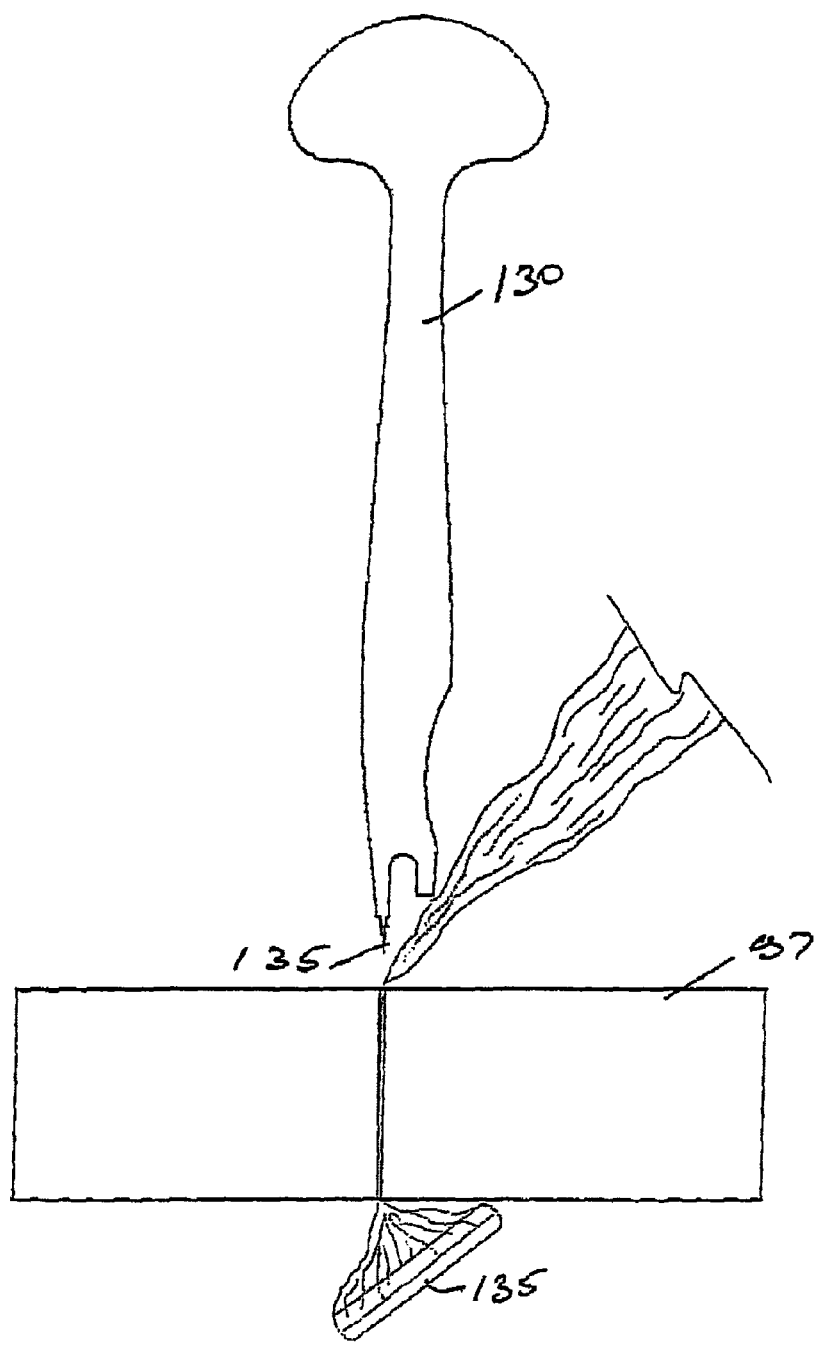

In some cases, as illustrated in FIGS. 41 and 42 an insertion tool 110 may have a stop 115 thereon to limit the extent by which the tool can project into the patient. The stop 115 may be fixed, or adjustable in position. The adjustment of the stop 115 may be used to facilitate different thicknesses of abdomen. Such adjustment could be achieved using any suitable means such as a screw thread or ratchet system. The adjustment may be rendered at least partially automatic by using a spring loaded type system.

An alternative insertion tool 120 is illustrated in FIGS. 43 to 46. In this case the leading end 121 of the tool 120 is blunted and is inserted through a pre-made incision 90. The distal ring 91 of the retractor is retained in a groove 122 at the distal end of the tool 120.

In an alternative embodiment illustrated in FIGS. 47 to 50 an introducer tool 130 has an integral blade 135 which is lined up to the desired location and the tool 130 is pushed through to make a leading incision 90 in the abdominal wall 97.

The introducer tool may be any suitable size, however it may be of a size similar to that of a conventional trocar i.e. typically 3 to 35 mm.

The invention is not limited to the embodiments hereinbefore described, with reference to the accompanying drawings, which may be varied in construction and detail.

The invention claimed is:

1. A wound retractor system comprising:
   a retractor having a retracting sleeve for insertion into a wound opening and a distal portion including a portion of the retracting sleeve and a distal ring, the portion of the retracting sleeve being attached continuously around the distal ring; and
   an insertion tool for inserting or assisting the insertion of or deployment of the distal portion such that the distal ring is located within a body cavity and the retracting sleeve lines the wound opening, the insertion tool including a groove configured to receive and hold the distal portion in an engaged position where the distal ring intersects a primary central longitudinal axis of the insertion tool, and the distal ring extends generally in a longitudinal direction with respect to the insertion tool.

2. A system as claimed in claim 1 wherein the distal ring is of flexible material.

3. A system as claimed in claim 1 wherein the distal ring is of elastomeric material.

4. A system as claimed in claim 1 wherein the insertion tool comprises an elongate member having a distal end.

5. A system as claimed in claim 4 wherein the distal end of the insertion tool has a cutting blade for penetrating the wound opening by piercing.

6. A system as claimed in claim 1 wherein the insertion tool comprises an enlarged proximal handle portion.

7. A system as claimed in claim 1 wherein the insertion tool has a wound engaging portion with a width of from 3 to 35 mm.

8. A system as claimed in claim 7 wherein the width of the wound engaging portion is from 5 to 12 mm.

9. A system as claimed in claim 1 wherein the wound retractor further comprises:
   a proximal member for location externally of a wound opening;
   the proximal member being movable to shorten an axial amount of the retracting sleeve between the proximal member and the distal ring to laterally retract a wound opening.

10. A system as claimed in claim 9 wherein the proximal member comprises one or more valves to facilitate sealed access of an object through the proximal member.

11. A system as claimed in claim 9 wherein the retracting sleeve is flared distally outwardly.

12. A system as claimed in claim 9 wherein the retractor includes a seal assembly to seal the wound opening.

13. A system as claimed in claim 12 wherein the seal assembly is provided externally of the wound opening.

14. A system as claimed in claim 12 wherein the seal assembly is mountable to the proximal member.

15. A system as claimed in claim 12 wherein the seal assembly includes a valve to facilitate sealed access of an object through the seal assembly.

16. A system as claimed in claim 15 wherein the object comprises an instrument.

17. A system as claimed in claim 9 wherein the proximal member comprises an annular ring assembly.

18. A system as claimed in claim 17 wherein the annular ring assembly comprises an inner ring and an outer ring, and the retracting sleeve extends between the inner ring and the outer ring.

19. A system as claimed in claim 18 wherein one of the inner ring or outer ring defines a projection for location in a complimentary recess of the outer ring, with the retracting sleeve located therebetween.

20. A system as claimed in claim 19 wherein the projection is locatable in the recess in a snap-fit manner.

21. A system as claimed in claim 19 wherein the inner ring defines the projection and the outer ring defines the recess.

22. A system as claimed in claim 19 wherein the outer ring defines the projection and the inner ring defines the recess.

23. A system as claimed in claim 1 wherein the distal ring comprises an O-ring.

24. A system as claimed in claim 1 wherein the distal ring comprises an annular disc.

25. A system as claimed in claim 1 wherein the distal ring is of a resilient material.

* * * * *